United States Patent
Wallace et al.

(10) Patent No.: US 8,702,695 B2
(45) Date of Patent: Apr. 22, 2014

(54) AUTO-ALIGNING ABLATING DEVICE AND METHOD OF USE

(75) Inventors: Michael P. Wallace, Pleasanton, CA (US); Robert Garabedian, Mountain View, CA (US); Brent Gerberding, San Jose, CA (US); Winnie Chung, San Francisco, CA (US); David S. Utley, Redwood City, CA (US)

(73) Assignee: Covidien LP, Mansfield, MA (US)

( * ) Notice: Subject to any disclaimer, the term of this patent is extended or adjusted under 35 U.S.C. 154(b) by 946 days.

(21) Appl. No.: 12/404,159

(22) Filed: Mar. 13, 2009

(65) Prior Publication Data
US 2009/0177194 A1 Jul. 9, 2009

Related U.S. Application Data

(60) Division of application No. 11/275,244, filed on Dec. 20, 2005, which is a continuation-in-part of application No. 11/286,257, filed on Nov. 23, 2005, now Pat. No. 7,959,627, and a continuation-in-part of application No. 11/286,444, filed on Nov. 23, 2005, now Pat. No. 7,997,278.

(51) Int. Cl.
*A61B 18/14* (2006.01)

(52) U.S. Cl.
USPC ............................................................ 606/41

(58) Field of Classification Search
USPC .............................. 606/41–50; 600/104, 127
See application file for complete search history.

(56) References Cited

U.S. PATENT DOCUMENTS

| | | |
|---|---|---|
| 552,832 A | 1/1896 | Fort |
| 1,798,902 A | 3/1931 | Raney |
| 3,517,128 A | 6/1970 | Hines |
| 3,901,241 A | 8/1975 | Allen, Jr. |
| 3,924,628 A | 12/1975 | Droegemueller et al. |
| 4,011,872 A | 3/1977 | Komiya |
| 4,196,724 A | 4/1980 | Wirt et al. |
| 4,304,239 A | 12/1981 | Perlin |
| 4,311,154 A | 1/1982 | Sterzer et al. |
| 4,407,298 A | 10/1983 | Lentz et al. |
| 4,411,266 A | 10/1983 | Cosman |
| 4,423,812 A | 1/1984 | Sato |
| 4,532,924 A | 8/1985 | Auth et al. |

(Continued)

FOREIGN PATENT DOCUMENTS

| | | |
|---|---|---|
| DE | 3838840 | 5/1990 |
| DE | 4303882 | 8/1994 |

(Continued)

OTHER PUBLICATIONS

Utley, David S.; U.S. Appl. No. 12/270,373 entitled "System and method for ablational treatment of uterine cervical neoplasma," filed Nov. 13, 2008.

(Continued)

*Primary Examiner* — Ronald Hupczey, Jr.

(57) ABSTRACT

An ablation device and methods for use thereof including a support structure adapted to support an ablation structure within an alimentary tract of a patient are provided. The support structure includes a longitudinal support with a longitudinal axis and a rotational support. The rotational support is adapted to permit at least part of the ablation structure to rotate with respect to the longitudinal support's longitudinal axis.

19 Claims, 12 Drawing Sheets

(56) References Cited

U.S. PATENT DOCUMENTS

| | | | |
|---|---|---|---|
| 4,565,200 | A | 1/1986 | Cosman |
| 4,640,298 | A | 2/1987 | Pless et al. |
| 4,658,836 | A | 4/1987 | Turner |
| 4,662,383 | A | 5/1987 | Sogawa et al. |
| 4,674,481 | A | 6/1987 | Boddie, Jr. et al. |
| 4,676,258 | A | 6/1987 | Inokuchi et al. |
| 4,705,041 | A | 11/1987 | Kim |
| 4,709,698 | A | 12/1987 | Johnston et al. |
| 4,740,207 | A | 4/1988 | Kreamer |
| 4,765,331 | A | 8/1988 | Petruzzi et al. |
| 4,776,349 | A | 10/1988 | Nashef et al. |
| 4,823,791 | A | 4/1989 | D'Amelio et al. |
| 4,860,744 | A | 8/1989 | Johnson et al. |
| 4,887,614 | A | 12/1989 | Shirakami et al. |
| 4,895,138 | A | 1/1990 | Yabe |
| 4,901,737 | A | 2/1990 | Toone |
| 4,906,203 | A | 3/1990 | Margrave et al. |
| 4,907,589 | A | 3/1990 | Cosman |
| 4,930,521 | A | 6/1990 | Metzger et al. |
| 4,943,290 | A | 7/1990 | Rexroth et al. |
| 4,947,842 | A | 8/1990 | Marchosky et al. |
| 4,949,147 | A | 8/1990 | Bacuvier |
| 4,955,377 | A | 9/1990 | Lennox et al. |
| 4,960,106 | A | 10/1990 | Kubokawa et al. |
| 4,966,597 | A | 10/1990 | Cosman |
| 4,969,890 | A | 11/1990 | Sugita et al. |
| 4,976,711 | A | 12/1990 | Parins et al. |
| 4,979,948 | A | 12/1990 | Geddes et al. |
| 4,998,539 | A | 3/1991 | Delsanti |
| 5,006,119 | A | 4/1991 | Acker et al. |
| 5,010,895 | A | 4/1991 | Maurer et al. |
| 5,019,075 | A | 5/1991 | Spears et al. |
| 5,035,696 | A | 7/1991 | Rydell |
| 5,045,056 | A | 9/1991 | Behl |
| 5,046,512 | A | 9/1991 | Murchie |
| 5,047,028 | A | 9/1991 | Qian |
| 5,056,532 | A | 10/1991 | Hull et al. |
| 5,057,107 | A | 10/1991 | Parins et al. |
| 5,078,717 | A | 1/1992 | Parins et al. |
| 5,083,565 | A | 1/1992 | Parins |
| 5,084,044 | A | 1/1992 | Quint |
| 5,088,979 | A | 2/1992 | Filipi et al. |
| 5,094,233 | A | 3/1992 | Brennan |
| 5,100,423 | A | 3/1992 | Fearnot |
| 5,106,360 | A | 4/1992 | Ishiwara et al. |
| 5,117,828 | A | 6/1992 | Metzger et al. |
| 5,122,137 | A | 6/1992 | Lennox |
| 5,125,928 | A | 6/1992 | Parins et al. |
| 5,151,100 | A | 9/1992 | Abele et al. |
| 5,156,151 | A | 10/1992 | Imran |
| 5,163,938 | A | 11/1992 | Kambara et al. |
| 5,171,299 | A | 12/1992 | Heitzmann et al. |
| 5,190,541 | A | 3/1993 | Abele et al. |
| 5,192,297 | A | 3/1993 | Hull |
| 5,197,963 | A | 3/1993 | Parins |
| 5,197,964 | A | 3/1993 | Parins |
| 5,205,287 | A | 4/1993 | Erbel et al. |
| 5,215,103 | A | 6/1993 | Desai |
| 5,232,444 | A | 8/1993 | Just et al. |
| 5,236,413 | A | 8/1993 | Fiering |
| 5,242,441 | A | 9/1993 | Avitall |
| 5,254,126 | A | 10/1993 | Filipi et al. |
| 5,255,679 | A | 10/1993 | Imran |
| 5,256,138 | A | 10/1993 | Vurek et al. |
| 5,257,451 | A | 11/1993 | Edwards et al. |
| 5,263,493 | A | 11/1993 | Avitall |
| 5,275,162 | A | 1/1994 | Edwards et al. |
| 5,275,169 | A | 1/1994 | Afromowitz et al. |
| 5,275,608 | A | 1/1994 | Forman et al. |
| 5,275,610 | A | 1/1994 | Eberbach |
| 5,277,201 | A | 1/1994 | Stern |
| 5,281,216 | A | 1/1994 | Klicek |
| 5,281,217 | A | 1/1994 | Edwards et al. |
| 5,281,218 | A | 1/1994 | Imran |
| 5,290,286 | A | 3/1994 | Parins |
| 5,292,321 | A | 3/1994 | Lee |
| 5,293,869 | A | 3/1994 | Edwards et al. |
| 5,305,696 | A | 4/1994 | Mendenhall |
| 5,309,910 | A | 5/1994 | Edwards et al. |
| 5,313,943 | A | 5/1994 | Houser et al. |
| 5,314,438 | A | 5/1994 | Shturman |
| 5,314,466 | A | 5/1994 | Stern et al. |
| 5,316,020 | A | 5/1994 | Truffer |
| 5,324,284 | A | 6/1994 | Imran |
| 5,328,467 | A | 7/1994 | Edwards et al. |
| 5,334,196 | A | 8/1994 | Scott et al. |
| 5,336,222 | A | 8/1994 | Durgin, Jr. et al. |
| 5,345,936 | A | 9/1994 | Pomeranz et al. |
| 5,348,554 | A | 9/1994 | Imran et al. |
| 5,363,861 | A | 11/1994 | Edwards et al. |
| 5,365,926 | A | 11/1994 | Desai |
| 5,365,945 | A | 11/1994 | Halstrom |
| 5,366,490 | A | 11/1994 | Edwards et al. |
| 5,368,557 | A | 11/1994 | Nita et al. |
| 5,368,592 | A | 11/1994 | Stern et al. |
| 5,370,675 | A | 12/1994 | Edwards et al. |
| 5,370,678 | A | 12/1994 | Edwards et al. |
| 5,372,138 | A | 12/1994 | Crowley et al. |
| 5,375,594 | A | 12/1994 | Cueva |
| 5,383,874 | A | 1/1995 | Jackson et al. |
| 5,383,876 | A | 1/1995 | Nardella |
| 5,383,917 | A | 1/1995 | Desai et al. |
| 5,385,544 | A | 1/1995 | Edwards et al. |
| 5,397,339 | A | 3/1995 | Desai |
| 5,398,683 | A | 3/1995 | Edwards et al. |
| 5,401,272 | A | 3/1995 | Perkins |
| 5,403,311 | A | 4/1995 | Abele et al. |
| 5,409,453 | A | 4/1995 | Lundquist et al. |
| 5,409,483 | A | 4/1995 | Campbell et al. |
| 5,411,025 | A | 5/1995 | Webster, Jr. |
| 5,413,573 | A | 5/1995 | Koivukangas |
| 5,415,657 | A | 5/1995 | Taymor-Luria |
| 5,421,819 | A | 6/1995 | Edwards et al. |
| 5,423,808 | A | 6/1995 | Edwards et al. |
| 5,423,811 | A | 6/1995 | Imran et al. |
| 5,423,812 | A | 6/1995 | Ellman et al. |
| 5,425,704 | A | 6/1995 | Sakurai et al. |
| 5,428,658 | A | 6/1995 | Oettinger et al. |
| 5,433,739 | A | 7/1995 | Sluijter et al. |
| 5,435,805 | A | 7/1995 | Edwards |
| 5,441,499 | A * | 8/1995 | Fritzsch ........................ 606/45 |
| 5,443,470 | A | 8/1995 | Stern et al. |
| 5,454,782 | A | 10/1995 | Perkins |
| 5,454,809 | A | 10/1995 | Janssen |
| 5,456,662 | A | 10/1995 | Edwards et al. |
| 5,456,682 | A | 10/1995 | Edwards et al. |
| 5,458,571 | A | 10/1995 | Lampropoulos et al. |
| 5,458,596 | A | 10/1995 | Lax et al. |
| 5,458,597 | A | 10/1995 | Edwards et al. |
| 5,462,545 | A | 10/1995 | Wang et al. |
| 5,465,717 | A | 11/1995 | Imran et al. |
| 5,470,308 | A | 11/1995 | Edwards et al. |
| 5,471,982 | A | 12/1995 | Edwards et al. |
| 5,472,441 | A | 12/1995 | Edwards et al. |
| 5,482,054 | A | 1/1996 | Slater |
| 5,484,400 | A | 1/1996 | Edwards et al. |
| 5,486,161 | A | 1/1996 | Lax et al. |
| 5,490,984 | A | 2/1996 | Freed |
| 5,496,271 | A | 3/1996 | Burton et al. |
| 5,496,311 | A | 3/1996 | Abele et al. |
| 5,500,012 | A | 3/1996 | Brucker et al. |
| 5,505,728 | A | 4/1996 | Ellman et al. |
| 5,505,730 | A | 4/1996 | Edwards |
| 5,507,743 | A | 4/1996 | Edwards et al. |
| 5,509,419 | A | 4/1996 | Edwards et al. |
| 5,514,130 | A | 5/1996 | Baker |
| 5,514,131 | A | 5/1996 | Edwards et al. |
| 5,517,989 | A | 5/1996 | Frisbie et al. |
| 5,520,684 | A | 5/1996 | Imran |
| 5,522,815 | A | 6/1996 | Burgin, Jr. et al. |
| 5,524,622 | A | 6/1996 | Wilson |
| 5,531,676 | A | 7/1996 | Edwards et al. |
| 5,531,677 | A | 7/1996 | Lundquist et al. |
| 5,533,958 | A | 7/1996 | Wilk |

(56) References Cited

U.S. PATENT DOCUMENTS

| | | |
|---|---|---|
| 5,536,240 A | 7/1996 | Edwards et al. |
| 5,536,267 A | 7/1996 | Edwards et al. |
| 5,540,655 A | 7/1996 | Edwards et al. |
| 5,542,916 A | 8/1996 | Hirsch et al. |
| 5,542,928 A | 8/1996 | Evans et al. |
| 5,549,644 A | 8/1996 | Lundquist et al. |
| 5,549,661 A | 8/1996 | Korkis et al. |
| RE35,330 E | 9/1996 | Malone et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,562,720 A | 10/1996 | Stern et al. |
| 5,566,221 A | 10/1996 | Smith et al. |
| 5,569,241 A | 10/1996 | Edwards |
| 5,571,116 A | 11/1996 | Bolanos et al. |
| 5,572,578 A | 11/1996 | Lin et al. |
| 5,578,007 A | 11/1996 | Imran |
| 5,588,432 A | 12/1996 | Crowley |
| 5,588,960 A | 12/1996 | Edwards et al. |
| 5,591,195 A | 1/1997 | Taheri et al. |
| 5,599,345 A | 2/1997 | Edwards et al. |
| 5,609,151 A | 3/1997 | Mulier et al. |
| 5,620,480 A | 4/1997 | Rudie |
| 5,621,780 A | 4/1997 | Smith et al. |
| 5,624,439 A | 4/1997 | Edwards et al. |
| 5,651,780 A | 7/1997 | Jackson et al. |
| 5,651,788 A | 7/1997 | Fleischer et al. |
| 5,658,278 A | 8/1997 | Imran et al. |
| 5,672,153 A | 9/1997 | Lax et al. |
| 5,676,674 A | 10/1997 | Bolanos et al. |
| 5,688,266 A | 11/1997 | Edwards et al. |
| 5,688,490 A | 11/1997 | Tournier et al. |
| 5,702,438 A | 12/1997 | Avitall |
| 5,709,224 A | 1/1998 | Behl et al. |
| 5,713,942 A | 2/1998 | Stern et al. |
| 5,716,410 A | 2/1998 | Wang et al. |
| 5,720,293 A | 2/1998 | Quinn et al. |
| 5,730,128 A | 3/1998 | Pomeranz et al. |
| 5,732,698 A | 3/1998 | Swanson et al. |
| 5,738,096 A | 4/1998 | Ben-Haim |
| 5,748,699 A | 5/1998 | Smith |
| 5,769,846 A | 6/1998 | Edwards et al. |
| 5,769,880 A | 6/1998 | Truckai et al. |
| 5,776,146 A * | 7/1998 | Sackier et al. ................ 606/142 |
| 5,779,698 A | 7/1998 | Clayman et al. |
| 5,797,835 A | 8/1998 | Green |
| 5,797,903 A | 8/1998 | Swanson et al. |
| 5,800,334 A | 9/1998 | Wilk |
| 5,800,429 A | 9/1998 | Edwards |
| 5,807,261 A | 9/1998 | Benaron et al. |
| 5,820,629 A | 10/1998 | Cox |
| 5,823,197 A | 10/1998 | Edwards |
| 5,823,955 A | 10/1998 | Kuck et al. |
| 5,827,273 A | 10/1998 | Edwards |
| 5,830,129 A | 11/1998 | Baer et al. |
| 5,830,213 A | 11/1998 | Panescu et al. |
| 5,833,688 A | 11/1998 | Sieben et al. |
| 5,836,874 A | 11/1998 | Swanson et al. |
| 5,842,984 A | 12/1998 | Avitall |
| 5,846,196 A | 12/1998 | Siekmeyer et al. |
| 5,860,974 A | 1/1999 | Abele |
| 5,861,036 A | 1/1999 | Godin |
| 5,863,291 A | 1/1999 | Schaer |
| 5,868,785 A | 2/1999 | Tal et al. |
| 5,871,483 A | 2/1999 | Jackson et al. |
| 5,876,340 A | 3/1999 | Tu et al. |
| 5,888,743 A | 3/1999 | Das |
| 5,891,134 A | 4/1999 | Goble et al. |
| 5,895,355 A | 4/1999 | Schaer |
| 5,902,263 A | 5/1999 | Patterson et al. |
| 5,904,711 A | 5/1999 | Flom et al. |
| 5,925,044 A | 7/1999 | Hofmann et al. |
| 5,938,694 A | 8/1999 | Jaraczewski et al. |
| 5,964,755 A | 10/1999 | Edwards |
| 5,976,129 A | 11/1999 | Desai |
| 5,984,861 A | 11/1999 | Crowley |
| 5,997,534 A | 12/1999 | Tu et al. |
| 6,004,262 A | 12/1999 | Putz et al. |
| 6,006,755 A | 12/1999 | Edwards |
| 6,010,511 A | 1/2000 | Murphy |
| 6,012,457 A | 1/2000 | Lesh |
| 6,016,437 A | 1/2000 | Tu et al. |
| 6,023,638 A | 2/2000 | Swanson et al. |
| 6,027,499 A | 2/2000 | Johnston et al. |
| 6,033,397 A | 3/2000 | Laufer et al. |
| 6,039,701 A | 3/2000 | Sliwa et al. |
| 6,041,260 A | 3/2000 | Stern et al. |
| 6,044,846 A | 4/2000 | Edwards |
| 6,053,172 A | 4/2000 | Hovda et al. |
| 6,053,913 A | 4/2000 | Tu et al. |
| 6,056,744 A | 5/2000 | Edwards |
| 6,059,719 A | 5/2000 | Yamamoto et al. |
| 6,068,629 A * | 5/2000 | Haissaguerre et al. ......... 606/41 |
| 6,071,277 A | 6/2000 | Farley et al. |
| 6,073,052 A | 6/2000 | Zelickson et al. |
| 6,086,558 A | 7/2000 | Bower et al. |
| 6,086,583 A | 7/2000 | Ouchi |
| 6,091,993 A | 7/2000 | Bouchier et al. |
| 6,091,995 A | 7/2000 | Ingle et al. |
| 6,092,528 A | 7/2000 | Edwards |
| 6,095,966 A | 8/2000 | Chornenky et al. |
| 6,096,054 A | 8/2000 | Wyzgala et al. |
| 6,102,908 A | 8/2000 | Tu et al. |
| 6,112,123 A | 8/2000 | Kelleher et al. |
| 6,117,101 A | 9/2000 | Diederich et al. |
| 6,120,434 A | 9/2000 | Kimura et al. |
| 6,123,703 A | 9/2000 | Tu et al. |
| 6,123,718 A | 9/2000 | Tu et al. |
| 6,138,046 A | 10/2000 | Dalton |
| 6,142,994 A | 11/2000 | Swanson et al. |
| 6,146,149 A | 11/2000 | Daound |
| 6,149,647 A | 11/2000 | Tu et al. |
| 6,162,237 A | 12/2000 | Chan |
| 6,179,836 B1 | 1/2001 | Eggers et al. |
| 6,182,666 B1 | 2/2001 | Dobak, III |
| 6,183,468 B1 | 2/2001 | Swanson et al. |
| 6,193,644 B1 | 2/2001 | Dobak, III et al. |
| 6,197,022 B1 | 3/2001 | Baker |
| 6,237,355 B1 | 5/2001 | Li |
| 6,238,392 B1 | 5/2001 | Long |
| 6,241,724 B1 | 6/2001 | Fleischman et al. |
| 6,245,065 B1 | 6/2001 | Panescu et al. |
| 6,254,598 B1 | 7/2001 | Edwards et al. |
| 6,258,087 B1 | 7/2001 | Edwards et al. |
| 6,258,118 B1 | 7/2001 | Baum et al. |
| 6,273,886 B1 | 8/2001 | Edwards et al. |
| 6,321,121 B1 | 11/2001 | Zelickson et al. |
| 6,325,798 B1 | 12/2001 | Edwards et al. |
| 6,325,800 B1 | 12/2001 | Durgin et al. |
| 6,338,726 B1 | 1/2002 | Edwards et al. |
| 6,355,031 B1 | 3/2002 | Edwards et al. |
| 6,355,032 B1 | 3/2002 | Hovda et al. |
| 6,358,245 B1 | 3/2002 | Edwards et al. |
| 6,363,937 B1 | 4/2002 | Hovda et al. |
| 6,383,181 B1 | 5/2002 | Johnston et al. |
| 6,394,949 B1 | 5/2002 | Crowley et al. |
| 6,402,744 B2 | 6/2002 | Edwards et al. |
| 6,405,732 B1 | 6/2002 | Edwards et al. |
| 6,409,723 B1 | 6/2002 | Edwards |
| H2037 H | 7/2002 | Yates et al. |
| 6,415,016 B1 | 7/2002 | Chornenky et al. |
| 6,416,511 B1 | 7/2002 | Lesh et al. |
| 6,423,058 B1 | 7/2002 | Edwards et al. |
| 6,425,877 B1 | 7/2002 | Edwards |
| 6,428,536 B2 | 8/2002 | Panescu et al. |
| 6,432,104 B1 | 8/2002 | Eurgin et al. |
| 6,440,128 B1 | 8/2002 | Edwards et al. |
| 6,448,658 B2 | 9/2002 | Takata et al. |
| 6,451,014 B1 | 9/2002 | Wakikaido et al. |
| 6,454,790 B1 | 9/2002 | Neuberger et al. |
| 6,464,697 B1 | 10/2002 | Edwards et al. |
| 6,468,272 B1 | 10/2002 | Koblish et al. |
| 6,514,246 B1 | 2/2003 | Swanson et al. |

(56) References Cited

U.S. PATENT DOCUMENTS

| | | |
|---|---|---|
| 6,514,249 B1 | 2/2003 | Maguire et al. |
| 6,535,768 B1 | 3/2003 | Baker et al. |
| 6,544,226 B1 | 4/2003 | Gaiser et al. |
| 6,547,776 B1 | 4/2003 | Gaiser et al. |
| 6,547,787 B1 | 4/2003 | Altman et al. |
| 6,551,302 B1 | 4/2003 | Rosinko et al. |
| 6,551,310 B1 | 4/2003 | Ganz et al. |
| 6,551,315 B2 * | 4/2003 | Kortenbach et al. ............ 606/46 |
| 6,562,034 B2 | 5/2003 | Edwards et al. |
| 6,572,578 B1 | 6/2003 | Blanchard |
| 6,572,610 B2 | 6/2003 | Kovalcheck et al. |
| 6,572,639 B1 | 6/2003 | Ingle et al. |
| 6,575,966 B2 | 6/2003 | Lane et al. |
| 6,589,238 B2 | 7/2003 | Edwards et al. |
| 6,613,047 B2 | 9/2003 | Edwards |
| 6,641,581 B2 | 11/2003 | Muzzammel |
| 6,663,626 B2 | 12/2003 | Truckai et al. |
| 6,673,070 B2 | 1/2004 | Edwards et al. |
| 6,682,528 B2 | 1/2004 | Frazier et al. |
| 6,689,130 B2 | 2/2004 | Arail et al. |
| 6,695,764 B2 | 2/2004 | Silverman et al. |
| 6,712,074 B2 | 3/2004 | Edwards et al. |
| 6,712,814 B2 | 3/2004 | Edwards et al. |
| 6,712,815 B2 | 3/2004 | Sampson et al. |
| 6,740,082 B2 | 5/2004 | Shadduck |
| 6,749,607 B2 | 6/2004 | Edwards et al. |
| 6,752,806 B2 | 6/2004 | Durgin et al. |
| 6,800,083 B2 | 10/2004 | Hiblar et al. |
| 6,837,886 B2 | 1/2005 | Collins et al. |
| 6,846,312 B2 | 1/2005 | Edwards et al. |
| 6,860,878 B2 * | 3/2005 | Brock ............................... 606/1 |
| 6,866,663 B2 | 3/2005 | Edwards et al. |
| 6,872,206 B2 | 3/2005 | Edwards et al. |
| 6,917,834 B2 | 7/2005 | Koblish et al. |
| 6,918,906 B2 | 7/2005 | Long |
| 6,923,808 B2 | 8/2005 | Taimisto |
| 6,929,642 B2 | 8/2005 | Xiao et al. |
| 6,953,469 B2 | 10/2005 | Ryan |
| 6,964,661 B2 | 11/2005 | Rioux et al. |
| 6,971,395 B2 | 12/2005 | Edwards et al. |
| 6,974,456 B2 | 12/2005 | Edwards et al. |
| 6,994,704 B2 | 2/2006 | Qin et al. |
| 7,004,938 B2 | 2/2006 | Ormsby et al. |
| 7,008,419 B2 | 3/2006 | Shadduck |
| 7,048,734 B1 | 5/2006 | Fleischman et al. |
| 7,056,320 B2 | 6/2006 | Utley et al. |
| 7,083,620 B2 * | 8/2006 | Jahns et al. ...................... 606/51 |
| 7,089,063 B2 | 8/2006 | Lesh et al. |
| 7,090,637 B2 | 8/2006 | Danitz et al. |
| 7,097,644 B2 | 8/2006 | Long |
| 7,122,031 B2 | 10/2006 | Edwards et al. |
| 7,125,407 B2 | 10/2006 | Edwards et al. |
| 7,150,745 B2 | 12/2006 | Stern et al. |
| 7,160,294 B2 | 1/2007 | Croft |
| 7,165,551 B2 | 1/2007 | Edwards |
| 7,167,758 B2 | 1/2007 | Baker et al. |
| 7,179,257 B2 | 2/2007 | West et al. |
| 7,293,563 B2 | 11/2007 | Utley et al. |
| 7,326,207 B2 | 2/2008 | Edwards |
| 7,329,254 B2 | 2/2008 | West et al. |
| 7,344,535 B2 | 3/2008 | Stern et al. |
| 7,347,860 B2 | 3/2008 | Ouchi |
| 7,351,201 B2 * | 4/2008 | Ouchi et al. ................... 600/104 |
| 7,416,549 B2 | 8/2008 | Young et al. |
| 7,425,212 B1 | 9/2008 | Danek et al. |
| 7,507,238 B2 | 3/2009 | Utley et al. |
| 7,507,239 B2 | 3/2009 | Shadduck |
| 7,530,979 B2 | 5/2009 | Ganz et al. |
| 7,556,628 B2 | 7/2009 | Utley et al. |
| 7,632,268 B2 | 12/2009 | Utley et al. |
| 7,850,685 B2 | 12/2010 | Kunis et al. |
| 7,959,627 B2 | 6/2011 | Utley et al. |
| 7,993,336 B2 | 8/2011 | Jackson et al. |
| 7,997,278 B2 | 8/2011 | Utley et al. |
| 8,012,149 B2 | 9/2011 | Jackson et al. |
| 2001/0041887 A1 | 11/2001 | Crowley |
| 2001/0051802 A1 | 12/2001 | Woloszko et al. |
| 2002/0068935 A1 | 6/2002 | Kortenbach |
| 2002/0087151 A1 | 7/2002 | Mody et al. |
| 2002/0128650 A1 | 9/2002 | McClurken |
| 2002/0177847 A1 | 11/2002 | Long |
| 2002/0183739 A1 | 12/2002 | Long |
| 2003/0069572 A1 | 4/2003 | Wellman et al. |
| 2003/0093117 A1 | 5/2003 | Saadat |
| 2003/0109837 A1 | 6/2003 | McBride-Sakal |
| 2003/0153905 A1 | 8/2003 | Edwards et al. |
| 2003/0158550 A1 | 8/2003 | Ganz et al. |
| 2003/0181900 A1 | 9/2003 | Long |
| 2003/0181905 A1 | 9/2003 | Long |
| 2003/0191512 A1 | 10/2003 | Laufer et al. |
| 2003/0216727 A1 | 11/2003 | Long |
| 2004/0073204 A1 | 4/2004 | Ryan et al. |
| 2004/0087936 A1 | 5/2004 | Stern et al. |
| 2004/0122452 A1 | 6/2004 | Deem et al. |
| 2004/0147916 A1 | 7/2004 | Baker |
| 2004/0153120 A1 | 8/2004 | Seifert et al. |
| 2004/0172016 A1 | 9/2004 | Bek et al. |
| 2004/0204708 A1 | 10/2004 | Edwards et al. |
| 2004/0215180 A1 | 10/2004 | Starkebaum et al. |
| 2004/0215235 A1 | 10/2004 | Jackson et al. |
| 2004/0215296 A1 | 10/2004 | Ganz et al. |
| 2004/0236316 A1 | 11/2004 | Danitz et al. |
| 2004/0243124 A1 | 12/2004 | Im et al. |
| 2004/0254571 A1 | 12/2004 | Iki et al. |
| 2005/0010162 A1 | 1/2005 | Utley et al. |
| 2005/0033271 A1 | 2/2005 | Qin et al. |
| 2005/0070978 A1 | 3/2005 | Bek et al. |
| 2005/0090817 A1 | 4/2005 | Phan |
| 2005/0096713 A1 | 5/2005 | Starkebaum et al. |
| 2005/0107829 A1 | 5/2005 | Edwards et al. |
| 2005/0143727 A1 | 6/2005 | Koblish et al. |
| 2005/0149013 A1 | 7/2005 | Lee |
| 2005/0154386 A1 | 7/2005 | West et al. |
| 2005/0159743 A1 | 7/2005 | Edwards et al. |
| 2005/0171524 A1 | 8/2005 | Stern et al. |
| 2005/0187546 A1 | 8/2005 | Bek et al. |
| 2005/0215983 A1 | 9/2005 | Brock |
| 2005/0228286 A1 | 10/2005 | Messerly et al. |
| 2005/0245926 A1 | 11/2005 | Edwards et al. |
| 2005/0288664 A1 | 12/2005 | Ford et al. |
| 2006/0009758 A1 | 1/2006 | Edwards et al. |
| 2006/0015162 A1 | 1/2006 | Edward et al. |
| 2006/0020276 A1 | 1/2006 | Saadat et al. |
| 2006/0041256 A1 | 2/2006 | Edwards et al. |
| 2006/0069303 A1 | 3/2006 | Couvillon |
| 2006/0086363 A1 | 4/2006 | Qin et al. |
| 2006/0095032 A1 | 5/2006 | Jackson et al. |
| 2006/0247614 A1 | 11/2006 | Sampson et al. |
| 2006/0259028 A1 | 11/2006 | Utley et al. |
| 2006/0259029 A1 | 11/2006 | Utley et al. |
| 2006/0259030 A1 | 11/2006 | Utley et al. |
| 2006/0282071 A1 | 12/2006 | Utley et al. |
| 2007/0066973 A1 | 3/2007 | Stern et al. |
| 2007/0100333 A1 | 5/2007 | Jackson et al. |
| 2007/0118104 A1 | 5/2007 | Wallace et al. |
| 2007/0118106 A1 | 5/2007 | Utley et al. |
| 2007/0118159 A1 | 5/2007 | Deem et al. |
| 2007/0135809 A1 | 6/2007 | Utley et al. |
| 2007/0142831 A1 | 6/2007 | Shadduck |
| 2007/0167963 A1 | 7/2007 | Deem et al. |
| 2007/0219570 A1 | 9/2007 | Deem et al. |
| 2008/0097427 A1 | 4/2008 | Stern et al. |
| 2008/0275445 A1 | 11/2008 | Kelly et al. |
| 2008/0319350 A1 | 12/2008 | Wallace et al. |
| 2009/0012512 A1 | 1/2009 | Utley et al. |
| 2009/0012513 A1 | 1/2009 | Utley et al. |
| 2009/0012518 A1 | 1/2009 | Utley et al. |
| 2009/0036733 A1 | 2/2009 | Wallace et al. |
| 2009/0036886 A1 | 2/2009 | Utley et al. |
| 2009/0048593 A1 | 2/2009 | Ganz et al. |
| 2009/0177194 A1 | 7/2009 | Wallace et al. |
| 2009/0318914 A1 | 12/2009 | Utley |

(56) References Cited

U.S. PATENT DOCUMENTS

| | | |
|---|---|---|
| 2010/0063495 A1 | 3/2010 | Utley et al. |
| 2010/0191237 A1 | 7/2010 | Shadduck |
| 2010/0234840 A1 | 9/2010 | Jackson et al. |
| 2011/0270249 A1 | 11/2011 | Utley |
| 2012/0239028 A1 | 9/2012 | Wallace et al. |

FOREIGN PATENT DOCUMENTS

| | | |
|---|---|---|
| EP | 0105677 | 4/1984 |
| EP | 0115420 | 8/1984 |
| EP | 0139607 | 5/1985 |
| EP | 0251745 | 1/1988 |
| EP | 0521595 A2 | 1/1993 |
| EP | 0608609 | 8/1994 |
| EP | 1323382 A1 | 7/2003 |
| EP | 1634542 B1 | 3/2006 |
| EP | 1769765 | 4/2007 |
| JP | H05-41509 U | 6/1993 |
| JP | 8-506738 | 7/1996 |
| JP | 2001120565 | 10/1999 |
| JP | 2004532064 | 3/2002 |
| JP | 2005503181 | 2/2005 |
| WO | WO 91/01773 | 2/1991 |
| WO | WO 91/03207 A1 | 3/1991 |
| WO | WO 92/10142 | 6/1992 |
| WO | WO 93/08755 | 5/1993 |
| WO | WO 94/07446 A1 | 4/1994 |
| WO | WO 94/10925 | 5/1994 |
| WO | 9421178 A1 | 9/1994 |
| WO | WO 94/21165 | 9/1994 |
| WO | WO 94/22366 | 10/1994 |
| WO | WO 94/26178 | 11/1994 |
| WO | WO 95/18575 | 7/1995 |
| WO | WO 95/19142 | 7/1995 |
| WO | WO 95/25472 | 9/1995 |
| WO | WO 96/00042 | 1/1996 |
| WO | WO 96/16606 | 6/1996 |
| WO | WO 96/29946 | 10/1996 |
| WO | WO 97/04702 | 2/1997 |
| WO | WO 97/06857 | 2/1997 |
| WO | WO 97/32532 | 9/1997 |
| WO | WO 97/43971 | 11/1997 |
| WO | WO 98/12999 A2 | 4/1998 |
| WO | WO 98/14238 A1 | 4/1998 |
| WO | WO 98/18393 A1 | 5/1998 |
| WO | WO 99/03413 | 1/1999 |
| WO | WO 99/35987 | 7/1999 |
| WO | WO 99/42046 | 8/1999 |
| WO | WO 99/55245 | 11/1999 |
| WO | WO 00/01313 | 1/2000 |
| WO | WO 00/59393 | 10/2000 |
| WO | WO 00/62699 A2 | 10/2000 |
| WO | WO 00/66017 A1 | 11/2000 |
| WO | WO 00/66021 | 11/2000 |
| WO | WO 00/66052 A1 | 11/2000 |
| WO | WO 00/69376 A1 | 11/2000 |
| WO | WO 01/22897 A1 | 4/2001 |
| WO | WO 01/35846 | 5/2001 |
| WO | WO 01/45550 A2 | 6/2001 |
| WO | WO 01/89440 | 11/2001 |
| WO | WO 02/096327 A2 | 12/2002 |
| WO | WO 03/015651 A1 | 2/2003 |
| WO | WO 03/070091 A1 | 8/2003 |
| WO | WO 2004/043280 A1 | 5/2004 |
| WO | WO 2007/001981 A2 | 1/2007 |
| WO | WO 2007/061984 A2 | 5/2007 |

OTHER PUBLICATIONS

Shadduck, John; U.S. Appl. No. 12/368,943 entitled "Surgical instruments and techniques for treating gastro-esophageal reflux disease," filed Feb. 10, 2009.

Wallace et al.; U.S. Appl. No. 12/404,159 entitled "Auto-aligning ablating device and method of use," filed Mar. 13, 2009.

Castell, D.O. Gastroesophageal Reflux Disease: Current Strategies for Patient Management. Arch Fam Med. 1996; 5(4):221-227.

Dallamagne et al; Laparoscopic Nissen Fundoplication: Preliminary. Surgical Laparoscopy and Endoscopy. 1991; 1(3):138-143.

Hinder et al; The Technique of Laparoscopic Nissen Fundoplication. Surgical Laparoscopy and Endoscopy. 1992; 2(3):265-272.

Kaneko et al; Physiological Laryngeal Pacemaker. Trans Am Soc. Artif Intern Organs. 1985; XXXI:293-296.

Karlstrom et al; Ectopic Jejunal Pacemakers and Enterogastric Reflux Roux Gastrectomy: Effect of Intestinal Pacing. Surgery. 1989; 106(3):486-495.

Kelly, K.A. et al; Duodenal-Gastric Reflux and Slowed Gastric Emptying by Electrical Pacing of the Canine Duodenal Pacesetter Potential. Gastroenterology. 1977; 72(3):429-433.

Mugica, et al. Direct Diaphragm Stimulation. PACE. 1987; 10:252-256.

Mugica, et al., Preliminary Test of a Muscular Diaphragm Pacing System on Human Patients. Neurostimulation: An Overview, chapter 21. 1985; 263-279.

Reynolds, J.C. Influence of Pathophysiology, Severity, and Cost on the Medical Management of Gastroesophageal Reflux Disease. Am J. Health-Syst Phar. 1996; 53(22su13):S5-S12.

Rice et al; Endoscopic Paranasal Sinus Surgery. Chapter 5, Functional Endoscopic Paranasal Sinus Surgery, The Technique of Messerklinger. Raven Press. 1988; 75-102.

Rice et al; Endoscopic Paranasal Sinus Surgery. Chapter 6, Total Endoscopic Sphenoethmoidectomy. The Technique of Wigand. Raven Press. 1988; 103-125.

Salameh et al; An Animal Model Study to Clarify and Investigate Endoscopic Tissue Coagulation by Using a New Monopolar Device. Gastrointestinal Endoscopy; 2004; 59 (1): 107-112.

Urshel, J.D. Complications of Antireflux Surgery. Am J. Surg. 1993; 166 (1):68-70.

Wallace et al.; U.S. Appl. No. 13/051,738 entitled "Selectively expandable operative element support structure and methods of use," filed Mar. 18, 2011.

Jackson et al.; U.S. Appl. No. 12/787,324 entitled "Methods and systems for determining physiologic characteristics for treatment of the esophagus," filed May 25, 2010.

Jackson, Jerome; U.S. Appl. No. 13/181,484 entitled "Methods and systems for treatment of tissue in a body lumen," filed Jul. 12, 2011.

Utley et al.; U.S. Appl. No. 13/181,490 entitled "Precision ablating method," filed Jul. 12, 2011.

Jackson et al.; U.S. Appl. No. 13/189,793 entitled "Methods and Systems for Determining Physiologic Characteristics for Treatment of the Esophagus," filed Jul. 25, 2011.

Shadduck, John H.; U.S. Appl. No. 12/751,803 entitled "Surgical instruments and techniques for treating gastro-esophageal reflux disease," filed Mar. 31, 2010.

DiabetesInControl.com, "How tummy surgery cures diabetes in a matter of days," (website accessed Jun. 6, 2007).

DiabetesInControl.com "How Tummy Surgery Cures Diabetes in a Matter of Days," (website accessed Jun. 6, 2007.

* cited by examiner

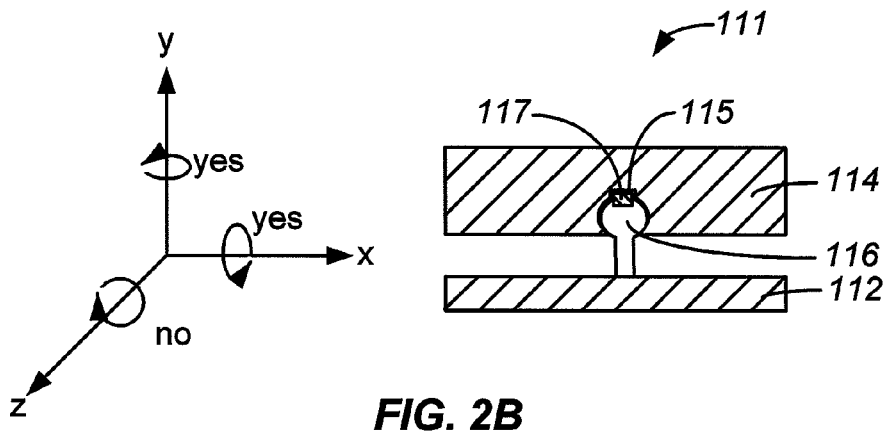
*FIG. 2B*
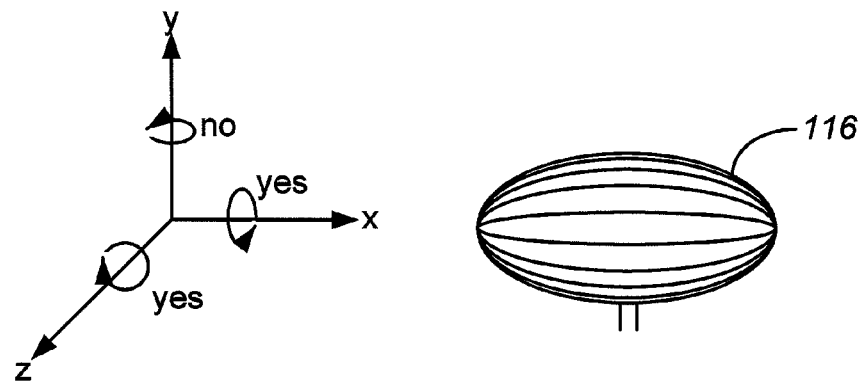
*FIG. 2C*
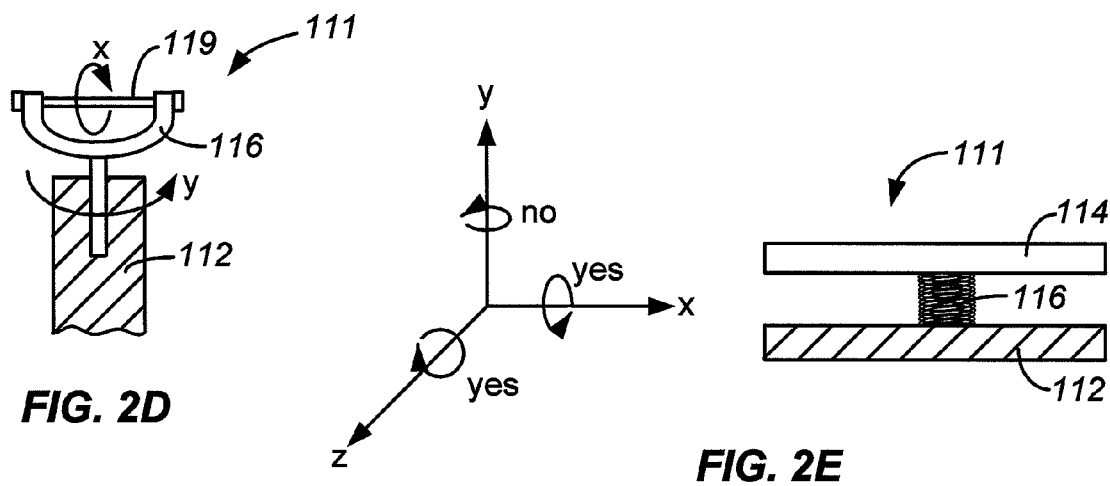
*FIG. 2D*
*FIG. 2E*

AUTO-ALIGNING ABLATING DEVICE AND METHOD OF USE

CROSS-REFERENCES TO RELATED APPLICATIONS

The present application is a divisional of U.S. patent application Ser. No. 11/275,244, filed Dec. 20, 2005, which is a continuation-in-part of commonly assigned, U.S. patent application Ser. No. 11/286,257, filed Nov. 23, 2005, now U.S. Pat. No. 7,959,627, and U.S. patent application Ser. No. 11/286,444, filed Nov. 23, 2005, now U.S. Pat. No. 7,997,278, the full disclosure of which are fully incorporated herein by reference.

FIELD OF THE INVENTION

The invention relates to medical devices and methods of use thereof, for ablating tissue in an alimentary tract.

BACKGROUND OF THE INVENTION

The primary function of the human esophagus is the transport of solid and liquid nourishment from the mouth to the stomach. The esophagus has inherent coordinated contractile capabilities, providing peristalsis of material in an antegrade direction (towards the stomach). Further, the esophagus secretes a neutral pH mucous to lubricate the passage of food, as well as to protect its lining from acid induced injury. The stomach contains a mixture of food and liquid from oral intake, acid and enzymes from the stomach lining, and bile and enzymes from the liver and pancreas. The lower esophageal sphincter and diaphragmatic muscles act as a valve at the junction of esophagus and stomach, preventing reflux of stomach contents into the esophagus. This lower esophageal sphincter normally remains closed until parasympathetic activation or approach of a food bolus causes its relaxation, allowing food to pass into the stomach from the esophagus. Distention of the stomach, particularly the cardiac portion of the stomach, causes an abrupt relaxation of the lower esophageal sphincter resulting in a venting event (belch). Certain foods, medication, and beverages containing caffeine or theophylline (xanthines) may predispose the lower esophageal sphincter to inappropriate relaxations, and subsequent reflux. Anatomical effects related to aging or hiatal hernia may also predispose a patient to reflux.

Patients having abnormal function of the lower esophageal sphincter may present with symptoms of dysphagia (difficulty in swallowing), heartburn due to reflux, chest pain, and other related symptoms. A common sign of chronic gastroesophageal reflux is erosive esophagitis. When chronically exposed to injurious stomach contents, the esophageal lining may breakdown leading to inflammation, erosion or ulceration. Chronic GERD and the resultant erosive esophagitis can lead to a pre-cancerous condition, known as Barrett's esophagus or intestinal metaplasia, which is injury-related genetic change in the epithelial cells.

As described for example in copending, commonly owned U.S. application Ser. No. 10/754,445, filed Jan. 9, 2004, a treatment catheter having an expandable electrode support can be used for treating a circumferential region of the esophagus in order to ablate an abnormal mucosal layer of the esophagus using radiofrequency (RF) energy. When successful, the treatment results in regeneration of a normal mucosal layer substantially free from metaplastic and other damaged epithelial cells characteristic of Barrett's esophagus.

In some instances, however, such radiofrequency ablation treatment may not be entirely successful and one or more regions of abnormal mucosa may remain. These focal areas may be approached with a device designed with a surface area more suited to ablating focal areas of mucosal disease. Further, some patients with Barrett's esophagus may present at baseline with very limited disease, either non-circumferential or very short segments that also would be better suited for focal ablation rather than circumferential ablation.

SUMMARY OF THE INVENTION

In general, in one aspect, the invention features an ablation device and methods of use thereof, including an ablation structure and a support structure adapted to support the ablation structure within an alimentary tract of a patient. The ablation device support structure includes, in one implementation, a longitudinal support with a longitudinal axis and a rotational support. The rotational support is adapted to permit at least a part of the ablation structure to move with respect to the longitudinal support's longitudinal axis.

Implementations of the invention can include one or more of the following features. The rotational support can be adapted to rotate with at least one degree of freedom. In an alternative implementation, the rotational support can be adapted to rotate with at least two degrees of freedom. In a further implementation, the rotational support can be adapted to rotate with at least three degrees of freedom.

The rotational support can include a stop member adapted to limit a range of rotational motion. The rotational support can include a movement resistor. In one implementation, the movement resistor includes a spring. In another implementation, the rotational support includes a lock adapted to prevent rotational movement of the ablation structure.

In one implementation the ablation device includes an actuator mechanism adapted to prevent rotational movement of the ablation structure.

The support structure can include an endoscope. Alternatively, the support structure includes a catheter.

The ablation structure can include at least one electrode. In one implementation, a plurality of ablation structures are supported by the support structure. In another implementation the ablation structure is capable of cryogenic tissue ablation.

In general, in another aspect, the invention features a method of ablating tissue in an alimentary tract including the steps of advancing an ablation structure into the alimentary tract; supporting the ablation structure with a support structure within the alimentary tract; rotating at least part of the ablation structure away from the support structure and toward a tissue surface; and activating the ablation structure to ablate the tissue surface.

Implementations of the invention can include a method of ablating tissue wherein the rotating step includes applying a force between the ablation structure and the tissue surface. In another implementation, the advancing an ablation structure step includes advancing a plurality of ablation structures, and the rotating step includes rotating at least part of one or more of the plurality of ablation structures by applying a force between one or more of the plurality of ablation structures and the tissue surface.

The rotating step can include rotating at least part of the ablation structure about at least one rotation axis. In one implementation, the rotating step includes rotating at least part of the ablation structure about at least two rotation axes.

In a further implementation, the rotating step includes rotating at least part of the ablation structure about at least three rotation axes.

In one implementation, the method of ablating tissue further includes limiting a rotation range of the ablation structure. In another implementation the method further includes resisting rotation of the ablation structure while rotating the ablation structure. In an additional implementation, the method further includes locking the ablation structure to prevent rotation of the ablation structure.

The step of advancing the ablation structure can include advancing an endoscope into the alimentary tract. In one implementation the supporting step includes supporting the ablation structure with the endoscope.

In one implementation the ablation structure includes at least one electrode, and the activating step includes supplying electrical energy to the electrode. In another implementation, the ablation structure is capable of cryogenic ablation, and the activating step includes supplying a super-cooled fluid to the ablation structure.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2B is a cross-section view of a structural support including an alternative rotational support and coordinate axes illustrating freedom of movement.

FIG. 2C is a view of an alternative rotational support including an alternative rotational support and coordinate axes illustrating freedom of movement.

FIG. 2D is a view of an alternative structural support including an alternative rotational support.

FIG. 2E is a view of an alternative structural support including an alternative rotational support and coordinate axes illustrating freedom of movement.

DETAILED DESCRIPTION OF THE INVENTION

Apparatus and methods for ablating tissue within an alimentary tract of a patient or subject, using an ablation device including a support structure adapted to support an ablation structure within the alimentary tract are provided. The support structure of the ablation device includes a longitudinal support having a longitudinal axis and a rotational support. The rotational support is adapted to permit at least a part of the ablation structure to rotate with respect to the longitudinal support's longitudinal axis. In accordance with the present invention, the ablation device is advanced into the alimentary tract. Optionally, the ablation device can be supported at the distal end of an endoscope. The ablation structure is rotationally deflectable toward a tissue surface and the ablation structure is activatable to ablate the tissue surface. Within the alimentary tract, variously sized tissue surface sites, can be selectively ablated using the apparatus and methods described herein.

For the purposes of this disclosure, any components made up of mucous membrane and muscle extending between the mouth and the anus; functioning in digestion and elimination are contemplated as part of the alimentary tract. Such components include but are not limited to the esophagus, stomach, small intestine, appendix, large intestine, colon, rectum and anal canal.

Figure 1:
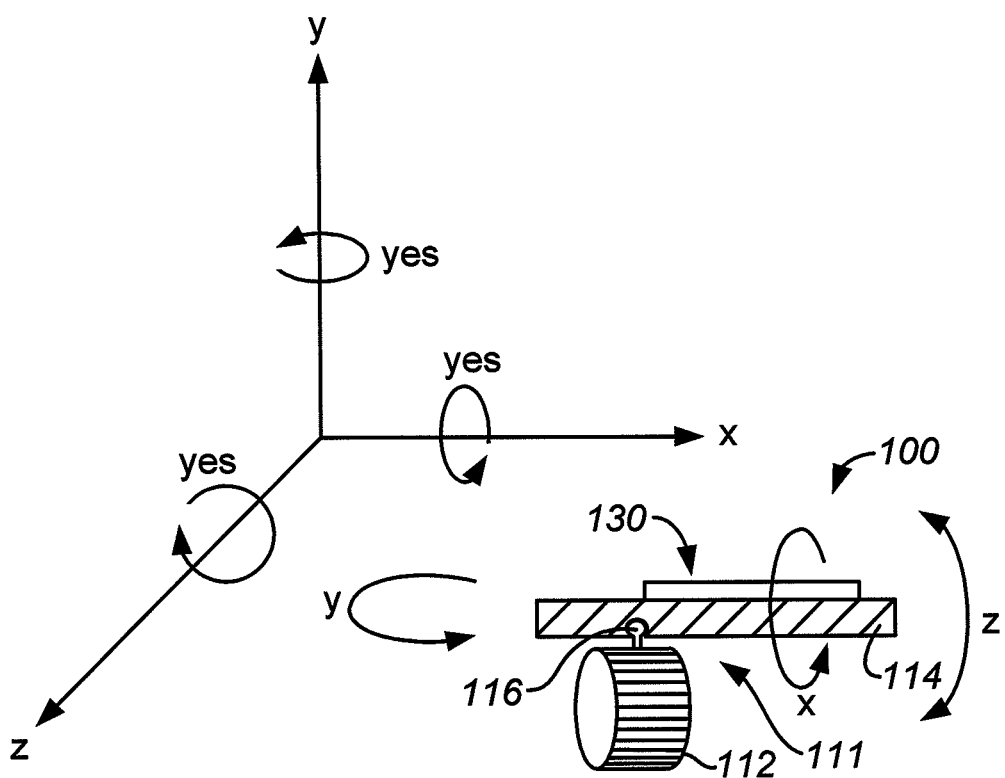
FIG. 1 is a view of the ablation device of the invention including coordinate axes illustrating freedom of movement.

As shown in FIG. 1, in general, the ablation device 100 of the invention includes a support structure 111 capable of supporting an ablation structure 130. The rotational support 116 includes a longitudinal support 114 that has a longitudinal axis and supports the ablation structure 130. The rotational support 116 is adapted to permit rotation of at least a part the longitudinal support 114 in relation to its longitudinal axis to permit at least a part of the ablation structure 130 to rotate. The longitudinal support 114 rotation as permitted by the rotational support includes but is not limited to, for example, rotating, pivoting, turning or spinning. It is envisioned that the longitudinal support 114 can be rotated away from, toward or along the support 114 longitudinal axis.

As further shown in FIG. 1 by a representation of the longitudinal structure 114 x, y and z coordinate axes, the rotational support 116 can permit the longitudinal structure 114 to move in several possible degrees of freedom. Although only a single arrowhead showing possible rotation about each axis is shown in FIG. 1 and subsequent figures, it is intended that bi-directional rotation about a given axis is represented.

Figure 2A:
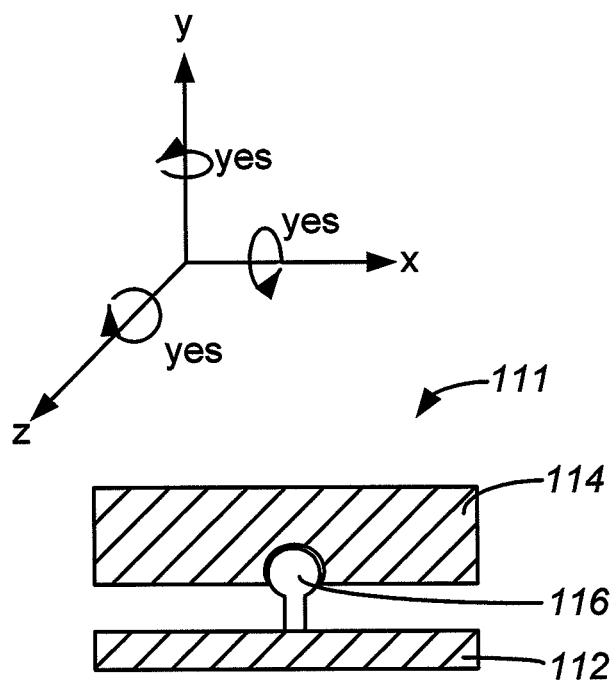
FIG. 2A is a cross-section view of a structural support including a rotational support and coordinate axes illustrating freedom of movement.

As shown in FIGS. 1 and 2A, the rotational support 116 can be constructed and arranged such that the longitudinal structure 114 is free to rotate with three degrees of freedom. The three degrees of freedom are indicated on the three axes, x, y, and z. In these and subsequent figures, a "yes"-labeled axis indicates bi-directional freedom of movement about the axis, whereas a "no"-labeled axis indicates no freedom of movement about the axis. It is envisioned that the rotational support can be adapted to rotate with at least one degree of freedom, with at least two degrees of freedom, or at least three degrees of freedom. It is further envisioned that the ablation device could be constructed and arranged to provide linear movement or a floating movement of the longitudinal structure along the x, y or z plane (not shown). For example, a sponge or compliant longitudinal support would allow for linear compression in the y direction (not shown).

As shown in FIGS. 2B-E, the rotational support 116 can be constructed and arranged such that the longitudinal structure 114 is free to rotate with two degrees of freedom. In the embodiments of FIGS. 2B and 2D, the longitudinal support is free to rotate about the x and y axes but not the z axis (see coordinate axes illustration in FIG. 2B and x and y axes indicated in FIG. 2D). In the embodiments shown in FIGS. 2C and 2E, the longitudinal support is free to rotate about the x and z axes but not the y axis.

Figure 5:
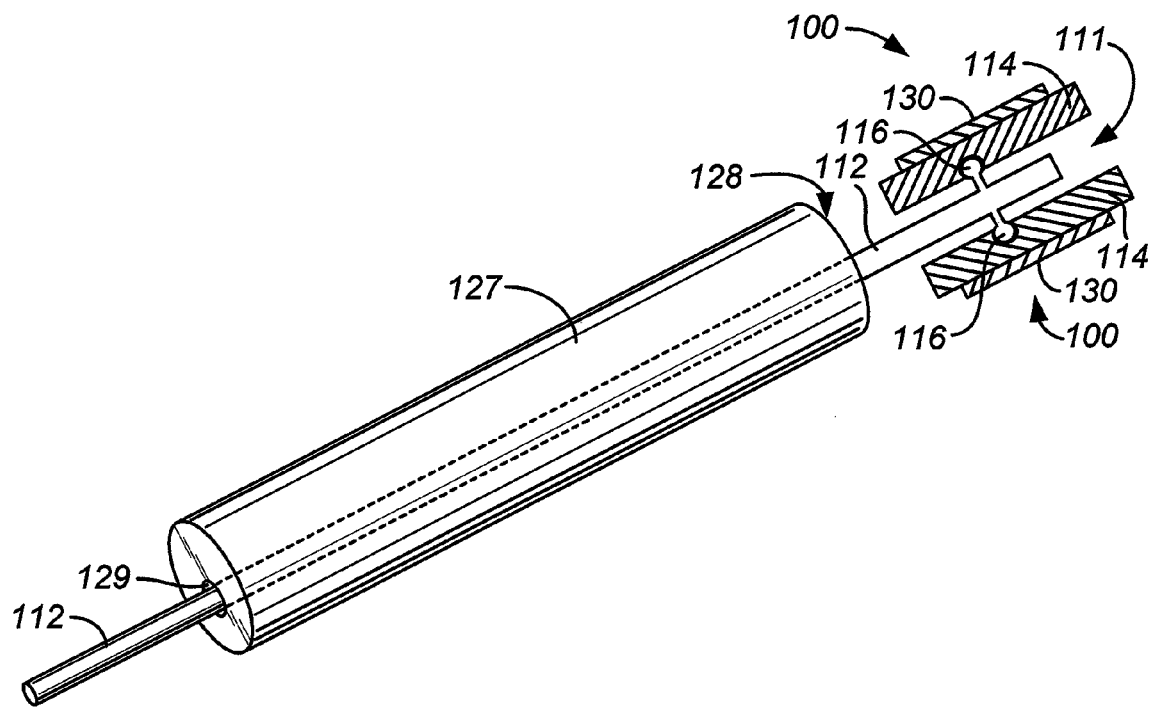
FIG. 5 is a view of the ablation device of the invention including a structural support with two rotational supports, two longitudinal supports, and tow ablation structures combined with an endoscope.

As shown in FIG. 5, the structural support 111 can include a single rotational support 116 coupled with two longitudinal supports 114, each supporting an ablation structure 130. The longitudinal support 114 and base 112 can be made of compliant materials including but not limited to silicones or urethanes. It is envisioned that the ablation device 100 can alternatively include two or more longitudinal supports 114 coupled with one or more rotational supports 114.

The rotational support can further include a base 112 portion as shown in FIGS. 1, 2A, 2B, 2D, 2E, 3A-C, 4A-B, 5, 6, 7A-B, 8A-B, 9A-B, 10, 11A-C, 12 and 14A-C. As discussed in detail below, in general, the base 112 is constructed and arranged to provide a means of attaching or connecting the ablation device 100 to an elongate member including but not limited to, for example, an endoscope or catheter.

A portion of the rotational support 116 can be constructed and arranged to include any of a number of shapes and structures for connecting the rotational support 116 to the longitudinal support 114 and providing rotational movement to the longitudinal support 114. Possible shapes include but are not limited to, for example, a rounded shape, a sphere, a constant diameter cylindrical shape, a variable diameter cylindrical shape and an oblong sphere shape. Possible structures include but are not limited to, for example, one or more hinge, spring, universal-joint, ball joint or pin joint.

As shown in FIGS. 1, 2A, 4B and 5, in one embodiment the rotational structure 116 can include a ball-shaped portion that can be set into a recess or receiver such as, for example, a socket in the longitudinal support 114. In another embodiment, as shown in FIG. 2B, the rotational structure 116 can include a ball-shaped portion having a projection 117 feature. In this embodiment the projection 117 engages a slot 115 feature of the longitudinal support 114 thereby permitting rotation of the longitudinal support 114 in two axes, the x and y axes, but not in the z axis. Engagement of the projection 117 with the slot 115 of the longitudinal support prohibits rotation of the longitudinal support 114 about the z axis.

In another embodiment, as shown in FIG. 2C, the rotational support 116 can include an elongate sphere or football-shaped portion. As indicated in the coordinate axes illustration, the embodiment depicted in FIG. 2C is constructed and arranged to permit rotation of the longitudinal support 114 (not shown) in relation to two axes. As shown, rotation of the longitudinal support 114 (not shown) can occur in the x and z axes but not in the y axis.

As shown in FIG. 2D, in yet another embodiment the support structure 111 can include a universal joint having a pin 119 and a rotational support 116. As indicated, this embodiment permits rotation of the longitudinal support 114 (not shown) in the x and y axes. It is envisioned that two or more universal joints could be included in the support structure 111. As shown in FIG. 2E, in a further embodiment the rotational structure 116 can includes a spring. As indicated in the coordinate axes illustration, this embodiment permits rotation of the longitudinal support 114 in the x and z axes but not in the y axis.

As shown in FIGS. 3A-C and 14A-C, in other embodiments the support structure 116 can include a structure comprising a pin 119. It is envisioned that the pin 119 can pass through a portion of the longitudinal support 114, the rotational support 116, and in some cases the base 112 (or connecting element 120 of the base 112) of the support structure 111, thereby connecting the longitudinal support 114 and the rotational support 116. Rotation about the pin 119 by the longitudinal support 114 provides rotation of at least a part the longitudinal support 114 in relation to its longitudinal axis. It is envisioned that one or more universal joints can be used in conjunction with one or more pins 119 to provide rotational movement to the longitudinal support (not shown).

Figure 14A:
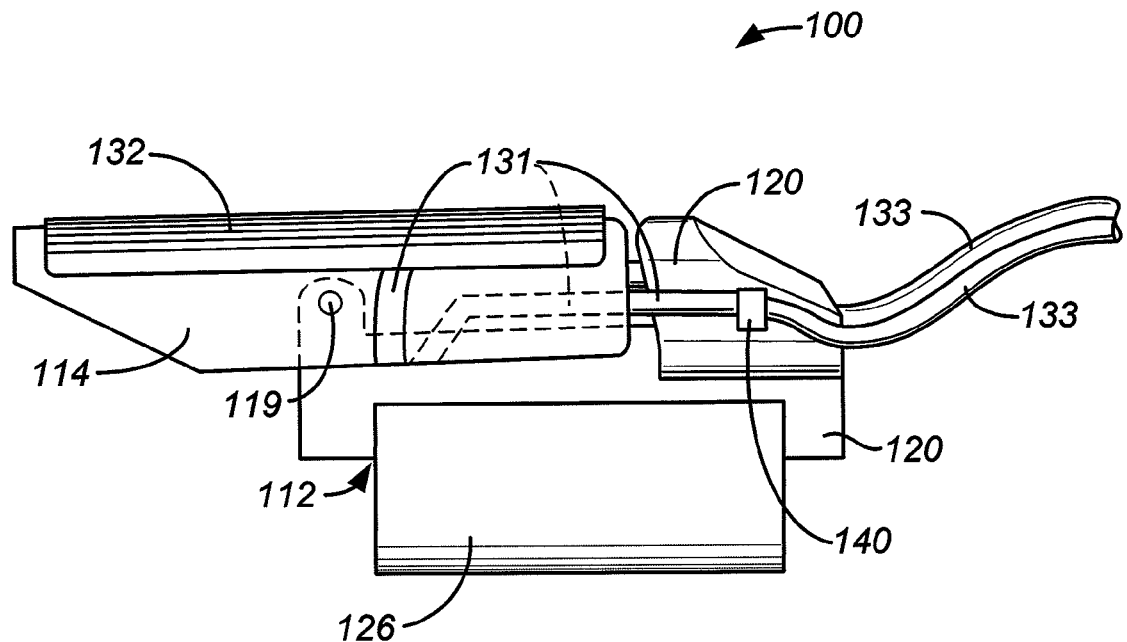
FIGS. 14A-B are views of an alternative embodiment of the ablation device.
Figure 14B:
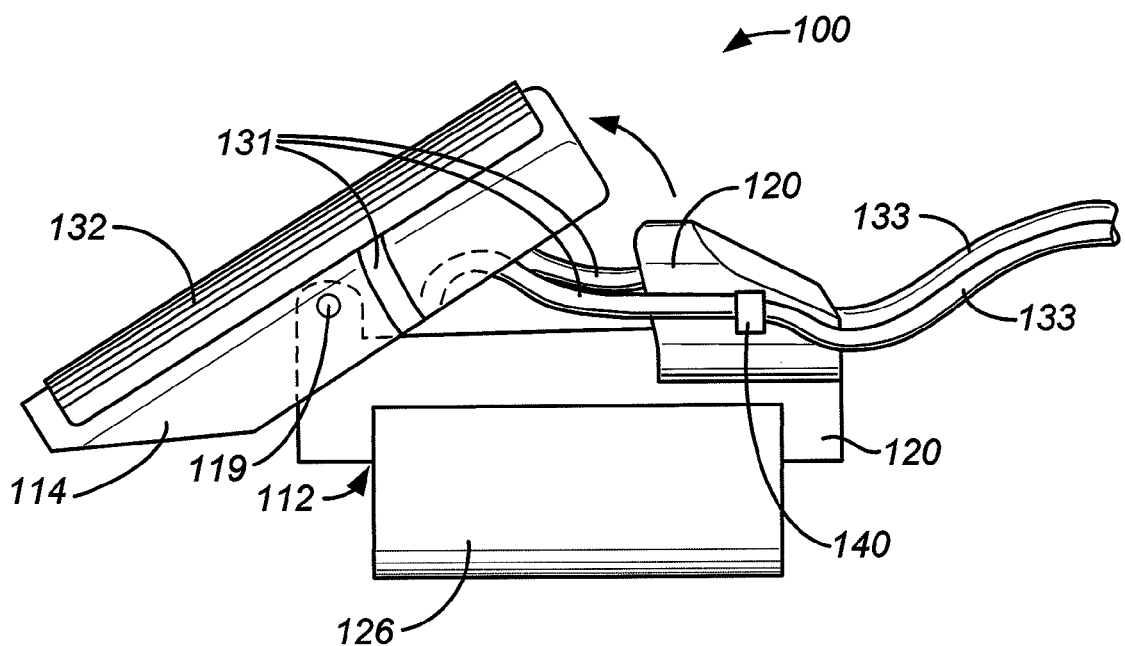

As shown in FIGS. 14A-B, where the support structure 116 comprises a pin 119, rotation of the longitudinal support 114 about the pin 119 can include a range of movement of the longitudinal support 114 from a neutral position (see FIG. 14A) to a tilted or angled position (see FIG. 14B). Both the neutral and angled positioning can be useful for treatment of a tissue surface. The neutral position, which includes a low profile, is particularly useful for introduction and/or removal of the ablation device 100 from a treatment site.

Figure 3A:
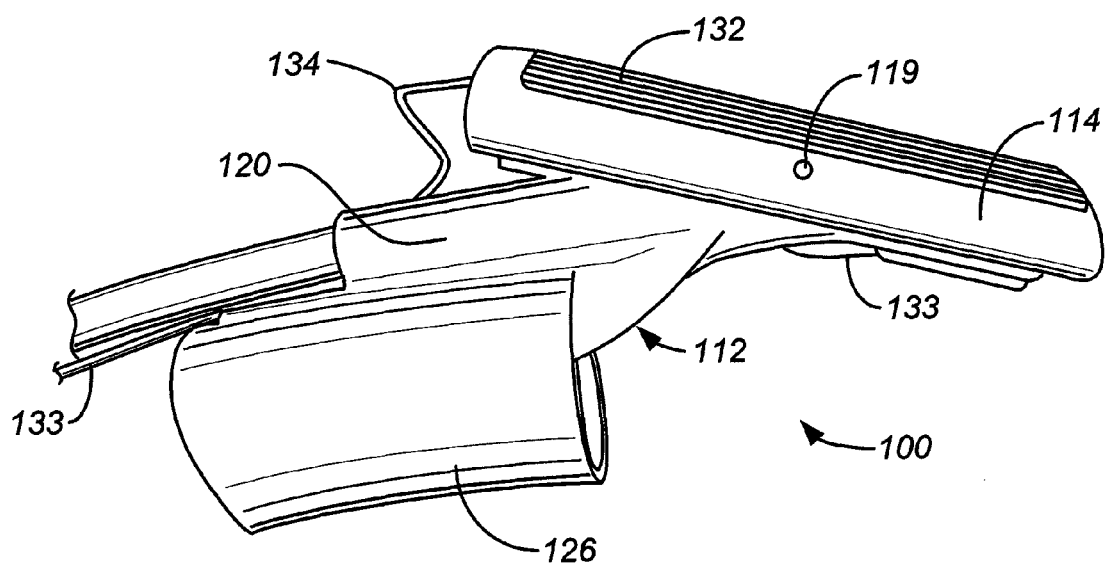
FIG. 3A is a view of the ablation device of the invention.
Figure 3B:
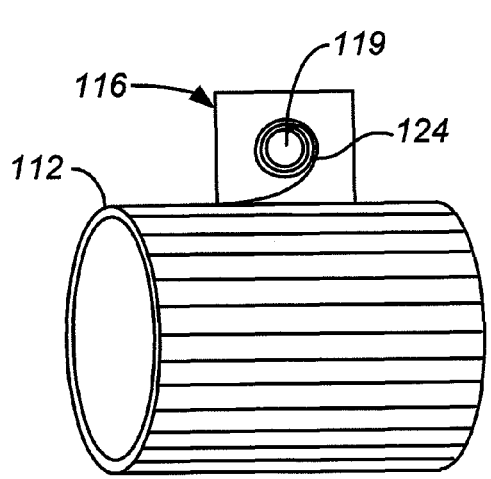
FIG. 3B is a view of an alternative rotational support.
Figure 3C:
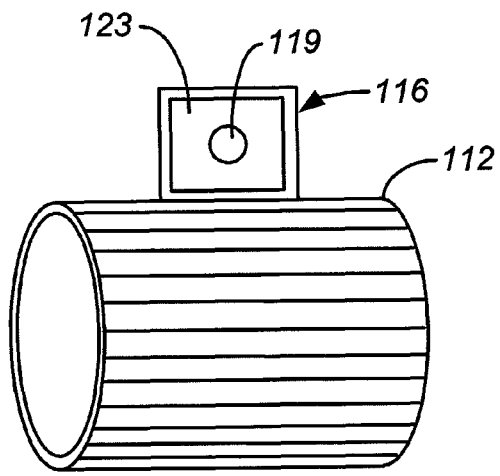
FIG. 3C is a view of another alternative rotational support.

As shown in FIG. 3B, in another embodiment the rotational support 116 in addition to including a pin 119 includes a spring 124 (e.g., a torsion spring) coupled to the pin 119. As shown in FIG. 3C, in yet another embodiment the rotational support 116 in addition to including a pin 119 includes a movement resistor 123 coupled to the pin 119. In this embodiment, the movement resistor 123 can be made up of any of a number of resistive or compliant substances or structures capable of returning the pin to a desired position after a period of pin 119 deflection or rotation. Suitable structures include but are not limited to sleeves or bushings, for example a silicone sleeve or bushing. Suitable materials for encasing or bonding a pin include but are not limited to silicone, urethane or other polymers. Other suitable materials and structures are well known to those of skill in the art.

It is envisioned that the structural support can include combinations of any of the rotational support 116 features described herein.

Figure 14C:
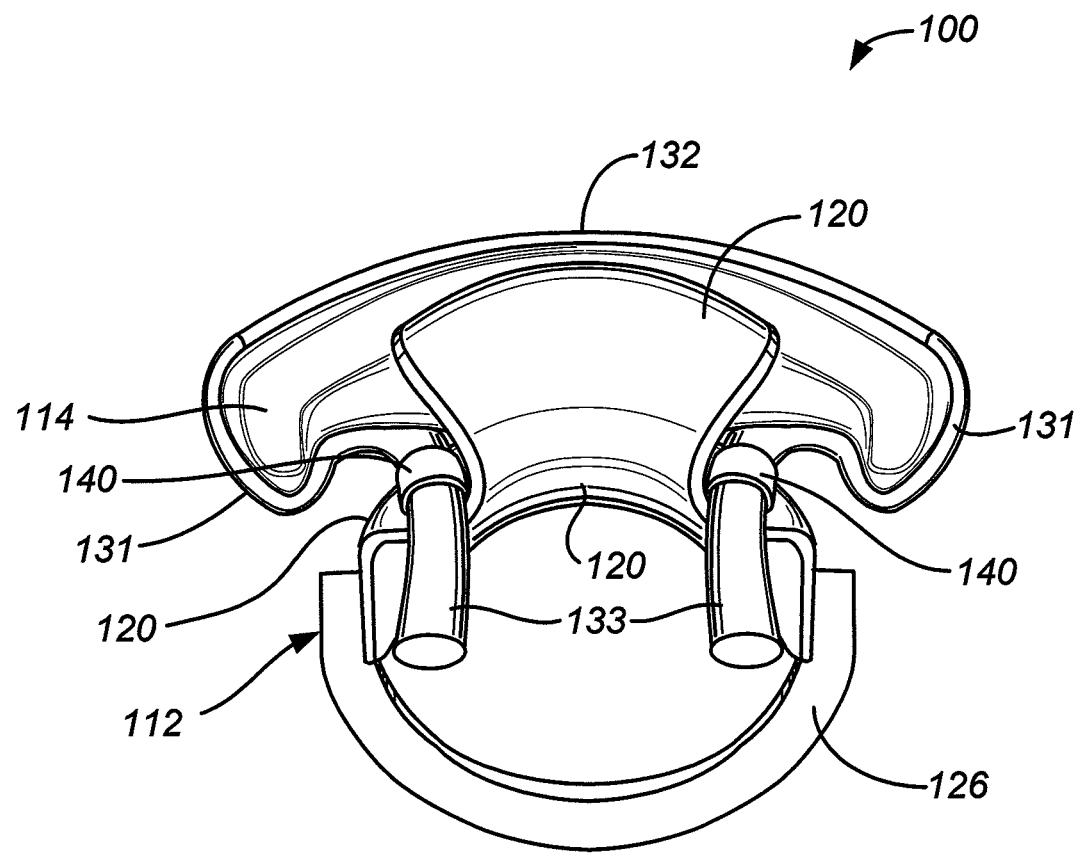
FIG. 14C is an end view of the ablation device shown in FIGS. 14A-B.

The base of the rotational support can be constructed and arranged in any of a number of ways to support the ablation device. In some embodiments, the base is constructed and arranged to connect the structural support of the ablation device to another device such as a conventional endoscope. For example, the base can be constructed and arranged to attach the ablation device to an outside surface of an endoscope. Alternatively, the base can be constructed and arranged to attach the ablation device to an inside surface, an outside or inside feature of an endoscope, or any combinations of the above. In some embodiments, as shown in FIGS. 1, 3B-C, 4A-B, 6, 7A-B, 8A-B, 9A-B, 10, 11A-B, and 12, the base 112 is constructed and arranged as a sheath. In a particular embodiment, the base 112 includes an elastomeric sheath. In other embodiments, as shown in FIGS. 3A and 14A-C, the base 112 includes a connecting element 120 and a band or strap 126. In one embodiment the strap 126 is an elastomeric strap. The connecting element 120 can provide an attachment point between the base 112 and the longitudinal support 114. The strap 126 can be attached to the connecting element 120 and function, for example, as a way of attaching an endoscope. The connecting element 120 and the strap 126 can be made up of the same or different materials if desired. As shown in FIGS. 14A-C, the connecting element 120 can include a tapered or sloped portion that angles up to the longitudinal support 114. As illustrated, in one embodiment the tapered portion of the connecting element 120 is positioned opposite to pin 119 on the connecting element 120 of the base 112. The tapered portion of the connecting element 120 can function to enable easy removal of the ablation device 100.

Figure 4A:
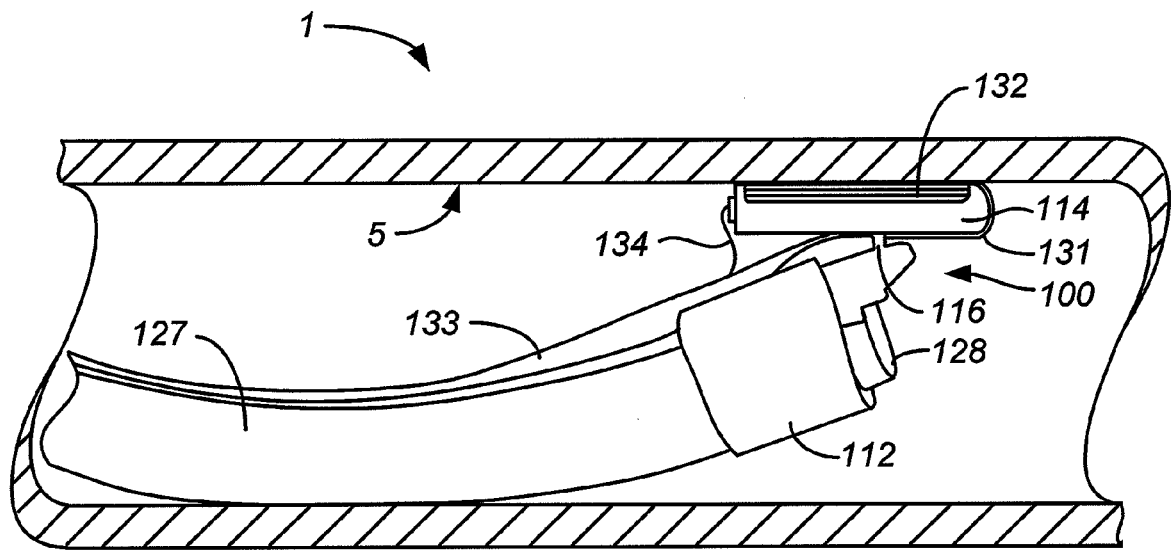
FIG. 4A is a view of the ablation device of the invention combined with an endoscope in the context of an alimentary tract.
Figure 4B:
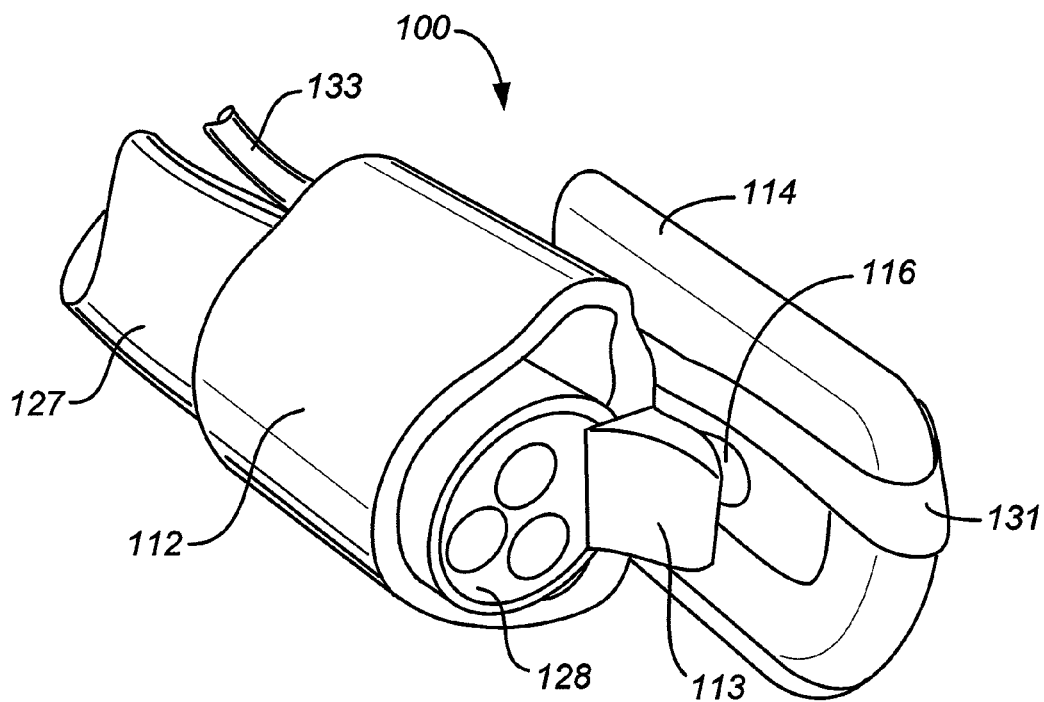
FIG. 4B is a view of the ablation device of the invention including a lip feature and an electrode trace combined with an endoscope.
Figure 4C:
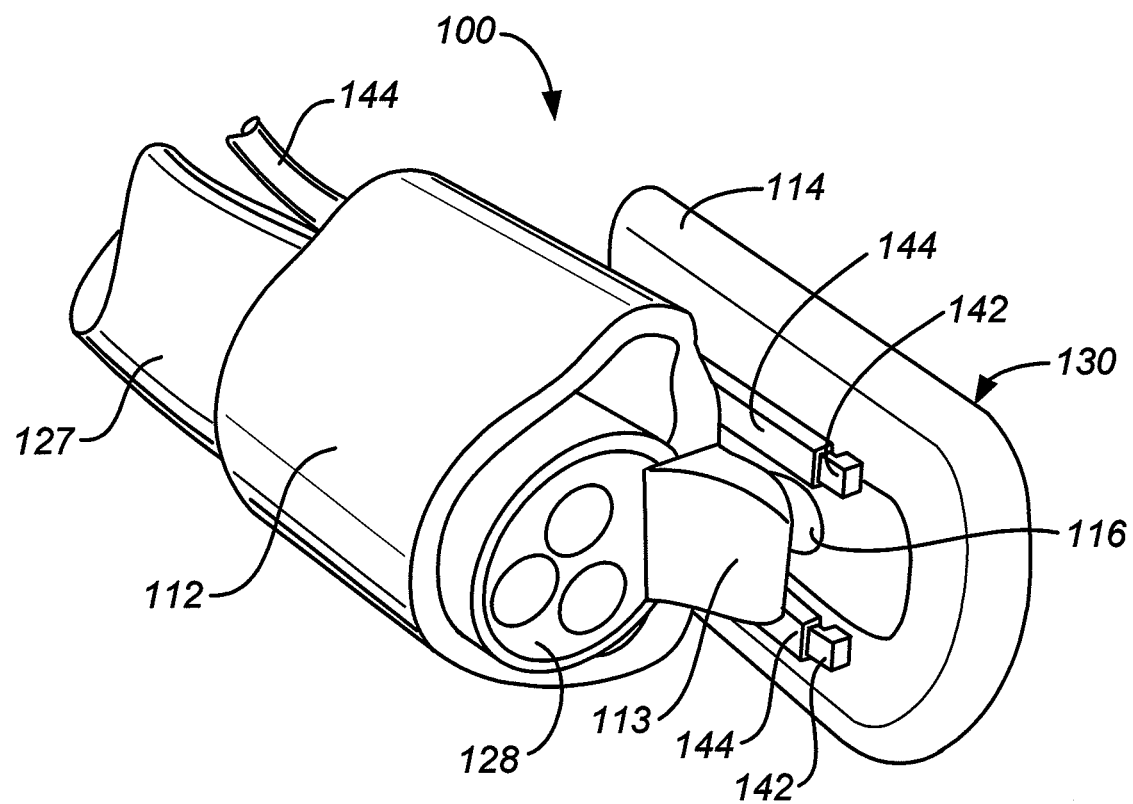
FIG. 4C is a view of the ablation device of the invention including a lip feature, ports and lines combined with an endoscope.

As shown in FIGS. 4B-C, in one embodiment rotational support base 112 includes a stop or lip 113 feature. The lip 113 can be constructed and arranged to function as a stop designed to aid in positioning the ablation device 100 in relation to an accessory device such as an endoscope 127 as shown. In the example shown in FIGS. 4B-C, positioning the endoscope 127 within the base 112 of the rotational support 116 can be limited by the lip 113. The lip 113 can index or limit the distal/proximal position of the ablation device 100 with respect to the endoscope distal end 128.

In general, in one aspect, the ablation device 100 includes a movement resistor 123 as shown in FIGS. 6, 7A-B, 8A-B, 9A-B, 10, 11A-C, and 12. In general, the movement resistor 123 is constructed and arranged to passively govern the rotational movement of the longitudinal support 114. Advantages of the movement resistor 123 include reduction of the profile of the ablation device 100. A reduced profile is useful when accessing and/or removing the ablation device 100 to and from a desired treatment area in a subject. For example, a reduced profile ablation device 100 can result in little or no lodging or catching of the device 100 upon access or removal from an alimentary tract 1. Because the longitudinal support 114 is generally free to move through one or more degrees of freedom, the movement resistor 123 can advantageously serve to govern freedom of movement. In some embodiments the movement resistor 123 includes an elastic or super elastic structure coupled with or attached to the longitudinal support 114. In other embodiments, the movement resistor 123 includes various other mechanical means to govern rotational movement of the longitudinal support 114.

Figure 6:
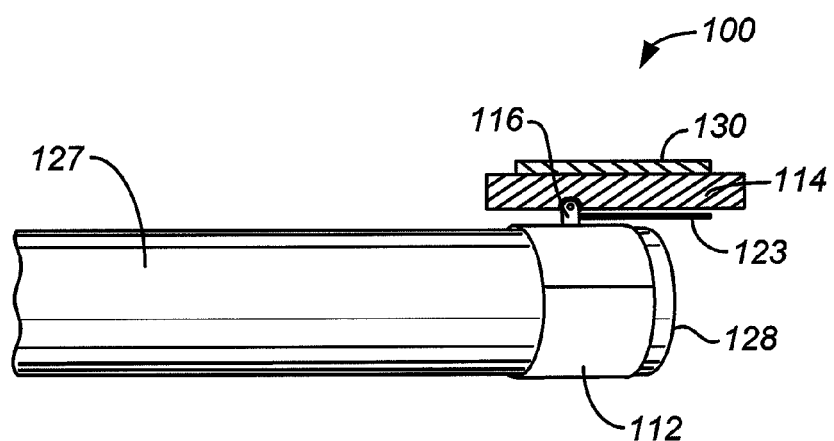
FIG. 6 is a view of the ablation device of the invention including a movement resistor.

As illustrated in FIG. 6, in one embodiment the movement resistor 123 includes a spring. It is envisioned that the spring can be a cantilever spring (as shown in FIG. 6), leaf spring, torsion spring or any of a number of spring types, all of which are well known to those of skill in the art. In one embodiment, as shown in FIG. 6, a cantilever spring movement resistor 123 can be constructed and arranged to restrict rotational movement of the longitudinal support 114 in relation to the distal end 128 of an attached endoscope 127. As illustrated, the longitudinal support 114 is generally maintained in a neutral position by the spring of the movement resistor 123. As used herein, "neutral position" means the longitudinal axis of the longitudinal support 114 is substantially parallel to a longitudinal axis of an endoscope 127 or other elongate member connected to the ablation device 100. In one embodiment, the movement resistor 123 is affixed to the rotational support base or the strap or connecting element of the base, so that it applies a pre-tension to the longitudinal support forcing the ablation device to be locked in its lowest profile position with respect to an attached endoscope 127 (not shown).

The movement resistor can be constructed and arranged to resist rotational movement of the longitudinal support and still permit force-induced rotational deflection of the longitudinal support away from the neutral position. In the absence of such force, some embodiments of the movement resistor tend to return to the longitudinal support to the neutral position. It is envisioned that the movement resistor can be constructed and arranged to affect rotational movement of the longitudinal support about one or more axes of movement. Furthermore, it is envisioned that different axes of movement (e.g., x, y and z axes; see FIG. 1) can be differentially affected by the movement resistor.

Figure 7A:
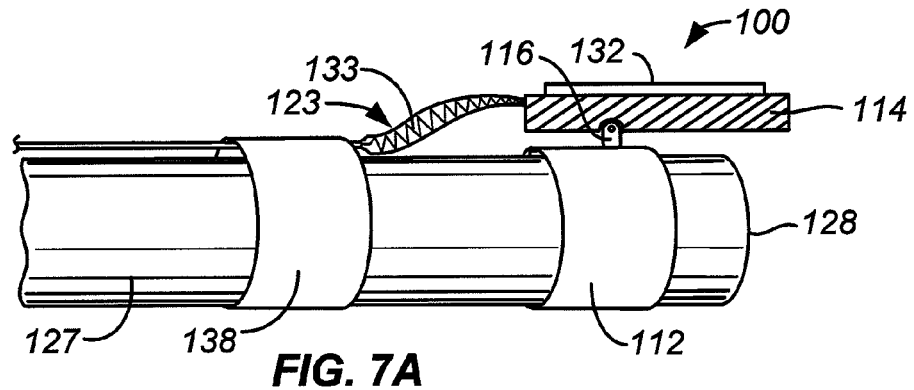
FIGS. 7A-B are views of the ablation device of the invention including an alternative movement resistor.
Figure 7B:
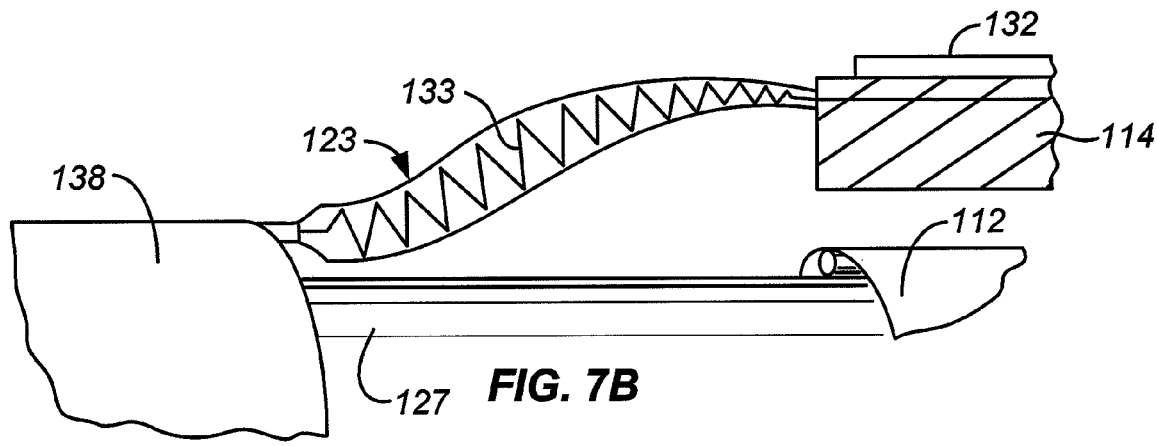

In another embodiment, as shown in FIGS. 7A-B, the movement resistor 123 can include a sheath encapsulating electrical conductive wires 133. The sheath can be made of an elastic or super elastic material, including but not limited to, for example, silicone. As shown in detail in FIG. 7B, the sheath movement resistor 123 is connected at one end to the longitudinal support 114. The opposite end of the sheath movement resistor 123 can be fixed in position relative to an endoscope 127 or other elongated structure by, for example, a sleeve 138 (see FIGS. 7A-B). In the embodiment shown in FIGS. 7A-B, the electrical conductive wires 133 can include a zigzag pattern. The pattern can permit lengthening of the electrical conductive wires 133 when the movement resistor 123 is lengthened.

Figure 8A:
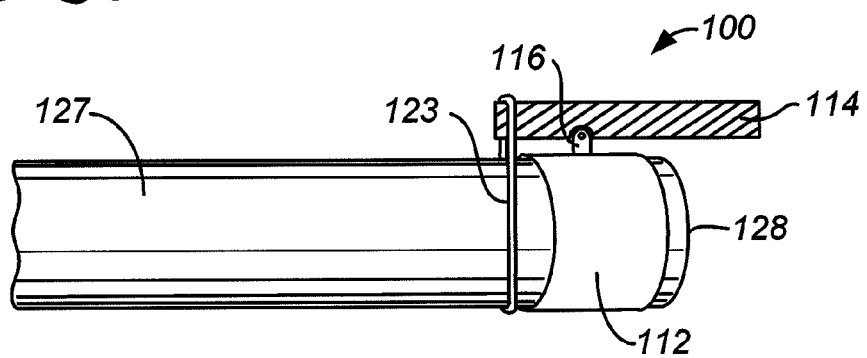
FIGS. 8A-B are views of the ablation device of the invention including alternative movement resistors.
Figure 8B:
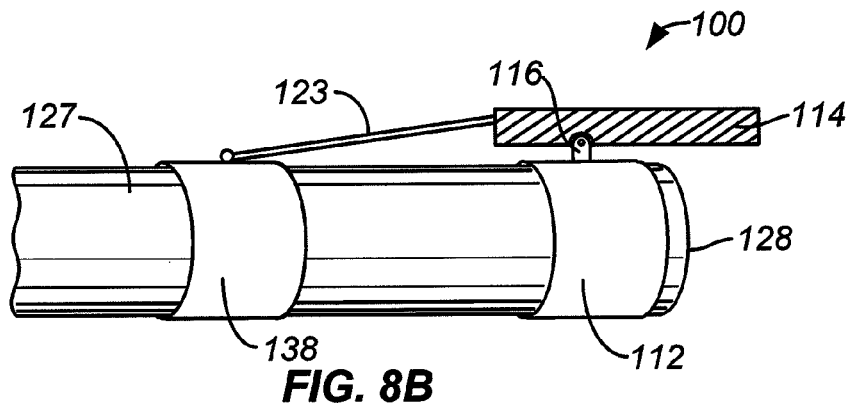

In yet another embodiment, as shown in FIGS. 8A-B, the movement resistor 123 can include a band of elastic or super elastic material coupled with or attached to the longitudinal support 114. Suitable elastic or super elastic materials can include but are not limited to silicone. As illustrated in FIG. 8A, in one embodiment the movement resistor is a band of elastic or super elastic material looped over and connecting a portion of the longitudinal support 114 with an endoscope 127. As illustrated in FIG. 8B, in another embodiment, the movement resistor 123 is a band of elastic or super elastic material connecting a portion of the longitudinal support 114 with an endoscope 127. In the example shown in FIG. 8B, the band is connected to the endoscope 127 by way of a sleeve 138 attached to the endoscope 127.

Figure 9A:
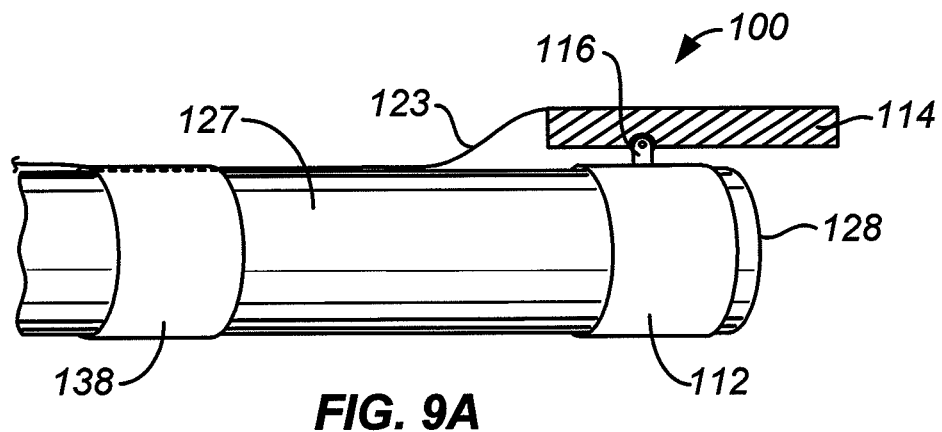
FIGS. 9A-B are views of the ablation device of the invention including alternative movement resistors.
Figure 9B:
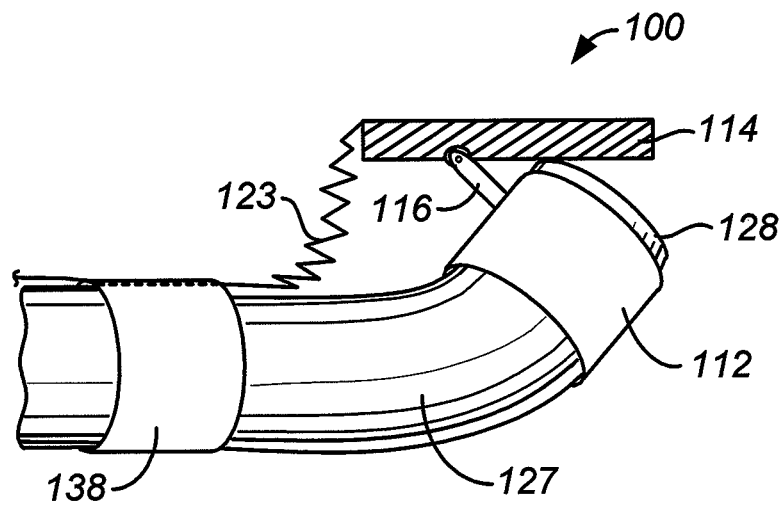

In a further embodiment, as shown in FIGS. 9A-B, the movement resistor 123 can include a stay or tether attached to a portion of the longitudinal support 114. A portion of the stay or tether can be connected to the endoscope 127 by way of a sleeve 138 attached to the endoscope 127. The movement resistor 123 of this embodiment can generally maintain the longitudinal support 114 in a neutral position when the distal end 128 of an endoscope 127 attached to the ablation device 100 is arranged in a relatively straight configuration. When the endoscope distal end 128 is deflected as shown in FIG. 9B, the stay or tether of the movement resistor 123 can slacken or gather on itself. In one embodiment the movement resistor 123 stay or tether is constructed and arranged such that upon slackening it collapse upon itself in an accordion-like manner (see FIG. 9B).

Figure 10:
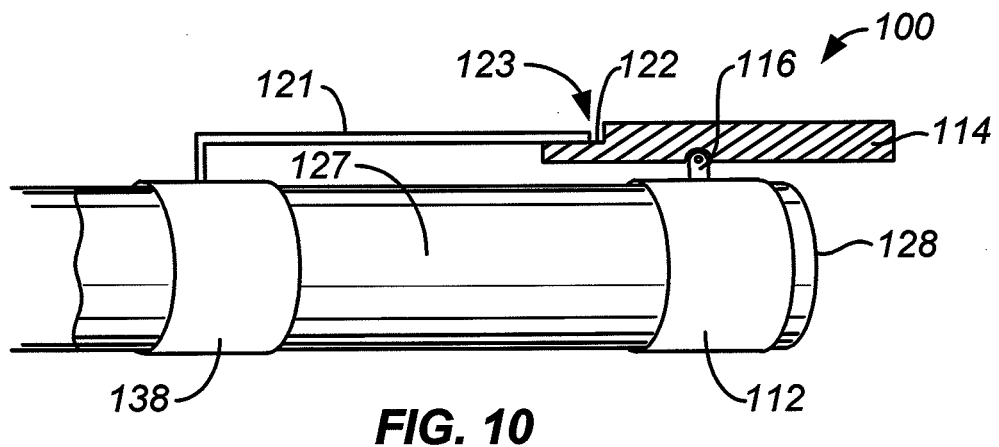
FIG. 10 is a view of the ablation device of the invention including alternative movement resistor.

In another embodiment, as shown in FIG. 10, the movement resistor 123 can include a finger 121 component, and a recess 122 component. The finger 121 can be connected to an endoscope 127 by way of a sleeve 138 or other attachment means, and the recess 122 can be included in the longitudinal support 114. As shown in FIG. 10, the finger 121 can engage the recess 122 thereby maintaining the longitudinal support 114 in a neutral position when the distal end 128 of an endoscope 127 attached to the ablation device 100 is arranged in a relatively straight configuration. The finger 121 and recess 122 can be constructed and arranged such that deflection of the endoscope distal end 128 or application of force to portions of the longitudinal support 114 can reversibly release the finger 121 from the recess 122. Once the finger 121 is released, the longitudinal support 114 is freed for rotational movement. Reconnection of the finger 121 and the recess 122 once again maintains the longitudinal support 114 in a neutral position.

Figure 11A:
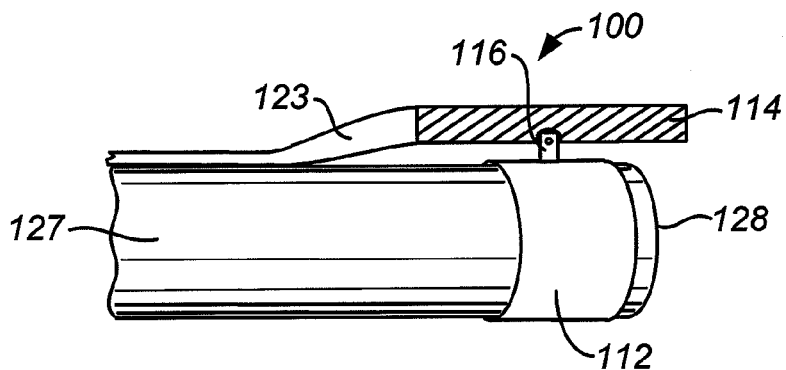
FIGS. 11A-C are views of the ablation device of the invention including alternative movement resistors.
Figure 11B:
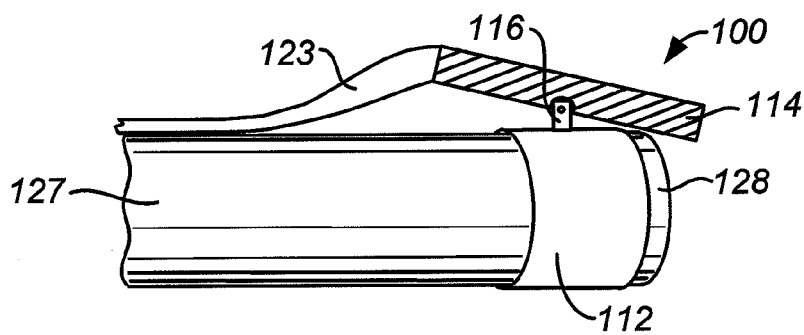
Figure 11C:
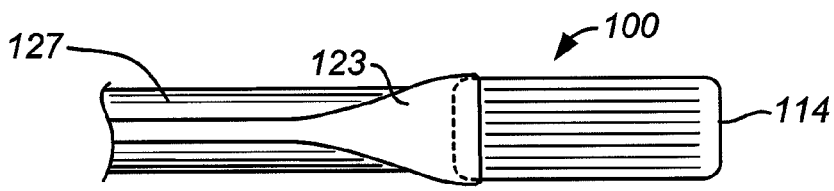

As shown in FIGS. 11A-C, in one embodiment the movement resistor 123 is a skirt or train connected to a portion of the longitudinal support 114 and extending proximally down the length of a connected endoscope 127. In this embodiment the skirt or train of the movement resistor 123 fits over a proximal end of the longitudinal support 114 or juxtaposition to the proximal end of 114. This arrangement provides a smooth profile to the proximal portion of the longitudinal support 144. Such a profile is useful for easing removal of the ablation device 100 from a treatment region by reducing the risk of the support 114 lodging or catching on a tissue surface. The movement resistor 123 can be attached to the longitudinal support 114 as shown in FIG. 11A or 11B to longitudinal support 114 or alternatively not be attached.

It is envisioned that one or more of the above described movement resistors can be included in a single ablation device to govern rotational movement of the longitudinal support. It is also envisioned that attachment of a portion of movement resistor to an endoscope, catheter or other structure can include any of a number of attachment means in addition to a sleeve attachment. For example, the movement resistor can be attached to an inside or outside surface of an endoscope or catheter or a feature thereof (not shown).

Figure 12:
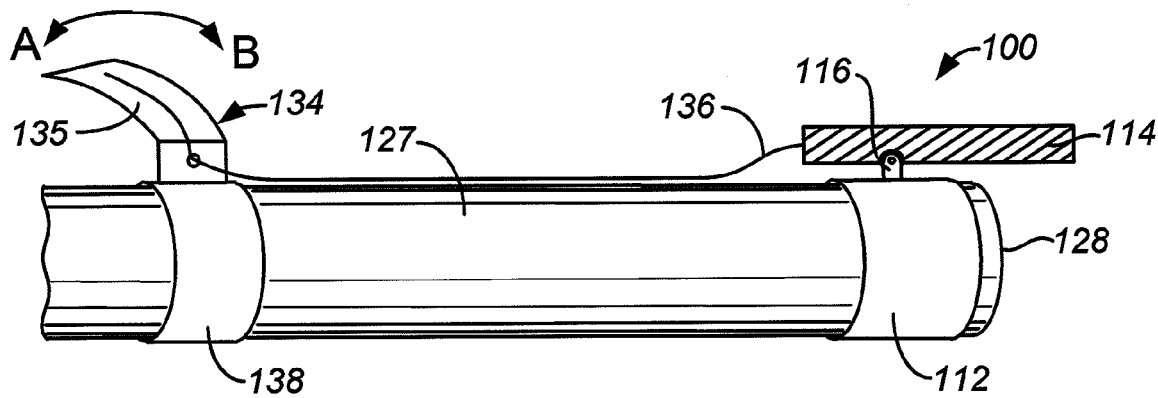
FIG. 12 is a view of the ablation device of the invention including an actuator mechanism.

In general, in one aspect, the ablation device 100 includes an actuator mechanism 134 for actively governing the rotation of the longitudinal support 114 (see e.g., FIG. 12). Generally the actuator mechanism 134 permits interconversion between a rotationally constrained longitudinal support 114 and free rotation of the support 114. As shown in FIG. 12, in one embodiment the actuator mechanism 134 includes a switch 135 and a stay 136 or tether. The switch 135 of the actuator mechanism 134 can be coupled to an endoscope 127 connected to the ablation device 100. The stay 136 can be connected to a portion of the longitudinal support 114. In the embodiment shown in FIG. 12, the switch 135 of the actuator mechanism 134 is attached to an endoscope by a sleeve 138 and can be positioned in one or more positions including the positions "A" and "B" as indicated. Switching the actuator mechanism 134 to position "A" causes the stay 136 to pull on and thereby immobilize the rotational freedom of the longitudinal support 114. Additionally, when in the "A" position, the support 114 is caused to be maintained in a neutral position. Switching the actuator mechanism 134 to position "B" relaxes the stay's 136 pull on the longitudinal support 114 thereby allowing for rotational movement of the support 114.

In another embodiment, the actuator mechanism includes a vacuum line (not shown). In this embodiment, rotational movement of the longitudinal support is governed by suction provided by a vacuum line constructed and arranged such that a proximal portion of the support can be immobilized when vacuum is applied. In the absence of the vacuum the longitudinal support would be able to rotate freely.

In yet another embodiment, the actuator mechanism is constructed and arranged such that rotational movement of the longitudinal support is governed by an electromagnet (not shown). In this embodiment, application of electromagnetic force causes immobilization of the longitudinal support in a neutral position. Accordingly, when the electromagnetic force is no long applied the support is able to rotate freely.

The ablation structure, in one embodiment is an electrode structure constructed and arranged to deliver energy comprising radiofrequency energy to tissue of an alimentary tract. It is envisioned that such an ablation structure can include a plurality of electrodes. For example, two or more electrodes can be part of an ablation structure. The energy may be delivered at appropriate levels to accomplish ablation of mucosal or submucosal level tissue, or alternatively to cause injury to these tissues, while substantially preserving muscularis tissue. The term "ablation" as used herein means thermal damage to the tissue causing tissue or cell necrosis. Thermal damage can be achieved through heating tissue or cooling tissue (i.e. freezing). Typically, ablation in the present embodiments is designed to remove the entire mucosal lining in the treatment region, including abnormal mucosa, for example, abnormal columnar growths, from the portions of the esophagus so affected, and allow re-growth of a normal mucosal lining. Advantageously, healing is more rapid and stricture formation in the tissues is minimized when such an approach is used. Also, the electrode ablation element could allow fluids such as saline to permeate through the longitudinal support and/or the electrode to prevent tissue sticking to the electrode during an ablation.

Although radiofrequency energy is one advantageous form of energy for ablation, it is recognized that other advantageous energy forms including, for example, microwave energy, or photonic or radiant sources such as infrared or ultraviolet light, the latter possibly in combination with improved sensitizing agents. Photonic sources can include semiconductor emitters, lasers, and other such sources. It is also recognized that another embodiment of this invention may utilize heatable fluid or a cooling media such as liquid nitrogen, Freon®, non CFC refrigerants or $CO_2$ as an ablation energy medium. For ablations using hot or cold fluids or gases, it is envisioned that the ablation system may require a means to circulate the heating/cool media from outside the patient to the heating/cooling balloon or other element and then back outside the patient again. Means for circulating media in cryosurgical probes are well known in the ablation arts. For example, and incorporated by reference herein, suitable circulating means are disclosed in U.S. Pat. No. 6,182,666 to Dobak, III; U.S. Pat. No. 6,237,355 to Li; and U.S. Pat. No. 6,572,610 to Kovalcheck et al.

The ablation structure can include a bipolar array of electrodes positioned on the structure capable of delivering radiofrequency energy in a bipolar fashion. Alternatively, the ablation structure may include a monopolar electrode structure can be energized by a radiofrequency power supply in combination with a return electrode typically positioned on the subject's skin, for example, on the small of the back. In either case, the radiofrequency energy can be delivered at a high energy flux over a very short period of time in order to injure or ablate only the mucosal or submucosal levels of tissue without substantially heating or otherwise damaging the muscularis tissue. Wherein the ablation structure includes a plurality of electrodes, one or more of the electrodes can be bipolar or monopolar. Combinations of bipolar and monopolar electrodes are envisioned.

As shown in FIGS. 1A, 3A, 4A, 5, 6, and 7A-B, the ablation structure 130 can be constructed and arranged in any of a number ways with regard to shape and size. As shown in FIGS. 3A, 4A, 7A-B and 14A-C, the ablation structure 130 can include an electrode array 132. Where the ablation structure 130 includes an electrode array 132, the array typically has an area in the range from substantially 0.5 cm² to 9.0 cm². Typical array shapes would include square, rectangular, circular or oval. In one embodiment, the ablation structure 101 has an area of 2.5 cm². In another embodiment, the ablation structure 101 has an area of 4 cm² and dimensions of 2 cm×2 cm.

The longitudinal support is constructed and arranged to support the ablation structure. The support 114 can be made of any suitable material for withstanding the high energy flux produced by the ablation structure 130. The longitudinal support can be flexible, enabling rotation about two axes, thereby further permitting rotation of the longitudinal support away from the longitudinal axis (not shown). In one embodiment the longitudinal support is made of an elastic material, for example, silicone. Other suitable materials include, for example, urethanes or other polymers.

As shown in FIGS. 3A, 4A-B, 7A-B and 14A-C, the ablation device 100 can further include electrical connections including conductive wires 133 to connect the ablation structure 130 to a power source. The conductive wires 133 can include a single wire or plurality of wires as needed to provide controlled energy delivery through the ablation structure. In one embodiment, the conductive wires 133 include low electrical loss wires such as litz wire. As shown in FIGS. 4A-B, the conductive wires 133 can be wrapped or drawn over a distal end of the longitudinal support 114 and pass beneath the support 114. Such an arrangement advantageously facilitates rotational movement of the longitudinal support 114 by preventing binding or restriction of rotational movement.

As shown in FIGS. 4A-B and 14A-C, the ablation device 100 can further include one or more electrode trace 131. The one or more electrode trace 131 can be constructed and arranged to conform to at least a portion of the longitudinal support 114. The one or more trace 131 can be in electrical communication with an electrode 132 and conductive wire 133. It is envisioned that the trace 131 can be an extension of electrode 132 or a separate element. As shown in FIGS. 14A-C, the one or more trace 131 can be in electrical communication with conductive wire 133 through a junction 140 feature. As shown, the junction 140 can be attached to the connecting element 120 of the base 112. It is envisioned that the conductive wires 133 can be removably connected to the ablation device by way of the junction 140 wherein the junction is constructed and arranged, for example, as an electrical connector.

It is also recognized that another embodiment of this invention may utilize heatable fluid or a cooling media such as liquid nitrogen, Freon®, non CFC refrigerants or $CO_2$ as an ablation energy medium. For ablations using hot or cold fluids or gases, it is envisioned that the ablation system may require a means to circulate the heating/cool media from outside the patient to the heating/cooling balloon or other element and then back outside the patient again. Means for circulating media in cryosurgical probes are well known in the ablation arts. For example, and incorporated by reference herein, suitable circulating means are disclosed in U.S. Pat. No. 6,182,666 to Dobak, III; U.S. Pat. No. 6,193,644 to Dobak, III et al.; U.S. Pat. No. 6,237,355 to Li; and U.S. Pat. No. 6,572,610 to Kovalcheck et al.

Accordingly, in another embodiment, as shown in FIG. 4C, the ablation structure 130 can be constructed and arranged for cryogenic ablation of tissue. In general, the longitudinal support 114 can support or serve as the ablation structure 130 by providing a conduit or support for the delivery of the cooling fluid to enable cryogenic ablation of tissue. In one implementation the ablation structure can be a balloon or balloon-like structure capable of being filled with fluid or gas (not shown). In another implementation, the ablation structure includes a capsule or box-like element covering a portion or all the surface of the longitudinal support, which can be filled with fluid or gas (not shown). In one implementation the longitudinal support is partially or completely hollow for receiving a fluid or gas. It is envisioned that the ablation structure or the longitudinal support can include a thermally conductive material for facilitating thermal transfer to effect cryogenic ablation of a tissue. It is also envisioned that the ablation structure or longitudinal support can include a thermally conductive feature covering all or a portion of its surface. For example, a suitable thermally conductive feature could be a thin metallic surface including but not limited to stainless steel or titanium.

It is envisioned that the ablation structure or longitudinal support can in some implementations are constructed and arranged to be permeable to heating or cooling agents (not shown). As such, it is further envisioned that the agent(s) can leach through the ablation structure or longitudinal support, thereby allowing for direct contact between the agent(s) and a tissue surface.

As shown in FIG. 4C, delivery of cooling fluid to the ablation structure 130 can include one or more line 144 and optionally one or more port 142. The line 144 can be constructed and arranged to transport fluid including super-cooled fluid. The port 142 can provide a connection between a line 144 and the ablation structure 130. The port 142 can be coupled directly to the longitudinal support 142. In one embodiment, the port is coupled to the longitudinal support and provides a conduit to an ablation structure associated with the support (not shown). Alternatively, the port 142 can be directly coupled to an ablation structure (not shown). In some implementations, line 144 is connected to the longitudinal support 114 by way of a port 142 (see FIG. 4C). The ports can include a nozzle or other features useful for producing a phase change in gas or liquid often accomplished through achieving pressure differential.

By way of example, as illustrated in FIG. 4C one implementation includes two lines 144 coupled with ports 142. The lines 144 both extend down the length of the attached endoscope 127 (only one line 144 visibly extends down the length of the endoscope 127 in the view shown in FIG. 4C). The ports 142 are directly connected to the underside of the longitudinal support 114 and the upper surface of the longitudinal support 114 serves as the ablation structure 130. The longitudinal support 114 can be substantially hollow to permit entry of an agent such as a heated or cooling fluid.

Optionally, the lines of the device can provide a return circuit for the flow of fluid to and from the ablation structure. For example, as shown in FIG. 4C, in one implementation where two lines 144 and two ports 142 are employed, one line 144 can serve as an input line while the other can serve as an outflow line.

In use, heated or super-cooled fluid can be delivered through the input line to the ablation structure, thereby activating the ablation structure. Activating the ablation structure with super-cooled fluid can include the induction of a phase change from liquid to gas or through generation of a pressure differential such as a pressure drop (given the Ideal Gas Law: PV=nRT). Cryogenic ablation of tissue can be achieved by contacting tissue with the super-cooled ablation structure. Optionally, a continuous flow of a heated or super-cooled fluid agent can be maintained in the ablation structure by continuous or discontinuous flow of the agent into the ablation structure and out through the outflow line. If desired, after ablation, the agent can be removed from the ablation structure. Optionally, after removal of the super-agent, another fluid, gas or air, having a desired temperature, can be introduced into the ablation structure.

In general, in another aspect a method of ablating tissue in an alimentary tract 1 includes advancing an ablation device 100 including an ablation structure 130 (here an electrode 132) into the alimentary tract 1 (see e.g., FIG. 4A). The ablation structure 130 is supported with a structural support 111 within the alimentary tract 1. At least a part of the ablation structure 130 can be rotated away from the structural support 111 and directed toward a tissue surface 5. The ablation structure 130 can be activated as desired to ablate the tissue surface 5.

As illustrated in FIG. 4A, in one embodiment, rotating at least part of the ablation structure 130 (shown here as an electrode 132) includes the application of force between the ablation structure 130, for example, an electrode 132 and the tissue surface 5. In another embodiment wherein the ablation device 100 includes multiple ablation structures 130 (see for example, FIG. 5) the rotating step includes applying force between one or more ablation structures 130 and the tissue surface 5.

The method of ablating tissue in an alimentary tract can further include rotating at least part of the ablation structure about at least one rotation axis, and/or about at least two rotation axes, and/or about at least three rotation axes. As discussed in detail above, the ablation device can be constructed and arranged to support such movement. For example, as shown in FIG. 1, the support structure 111 of the ablation apparatus 100 can include a longitudinal support 114 and a rotational support 116. The ablation structure 130 is supported by the longitudinal support 114, while the rotational support 116 is adapted to permit rotation of at least part of the ablation structure 130. Various structural aspects relating to rotational movement of the ablation structure 130 of the present method are discussed in detail above.

In another embodiment, the method of rotating at least part of the ablation structure includes limiting the range of rotation of the ablation structure. Various structural aspects of features relating to limiting the range of rotation in x, y and z axes are discussed above. For example, various rotational supports are disclosed as providing degrees of freedom of movement in relation to x, y and z axes.

In a further embodiment, the method includes resisting rotation of the ablation structure while rotating the structure. As discussed above, the ablation device can include various movement resistor structural features constructed and arranged to resist rotational movement of the ablation structure. For example, movement resistors are disclosed that govern rotational movement of the longitudinal support and thereby the ablation structure.

Figure 13:
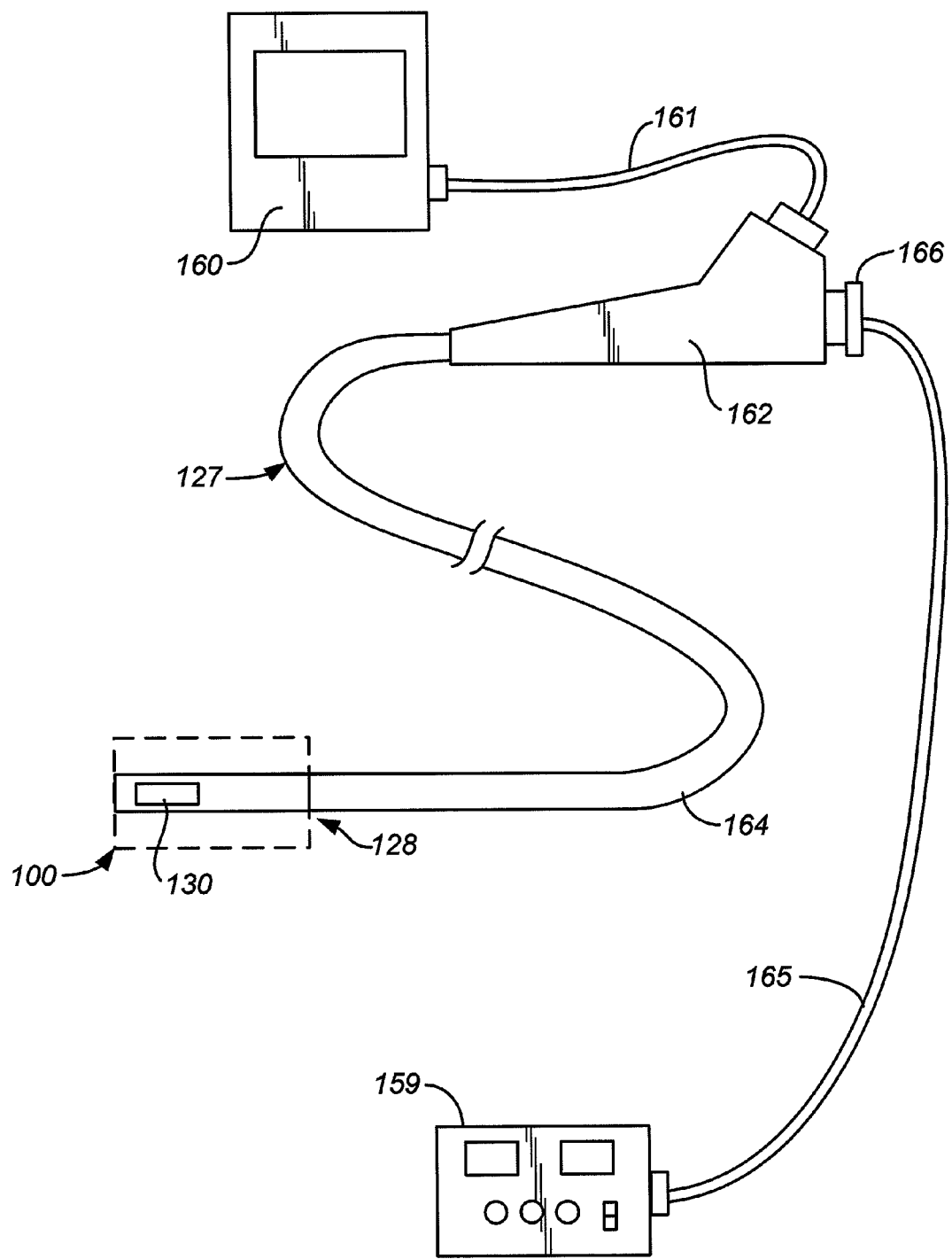
FIG. 13 is a view of the ablation device of the invention connected to an endoscope.

In one embodiment, as illustrated in FIG. 4A, the step of advancing the ablation structure 130 comprises advancing an endoscope 127 into the alimentary tract 1. An example of one commercially available conventional endoscope 127 is the Olympus "gastrovideoscope" model number GIF-Q160. While the specific construction of particular commercially available endoscopes may vary, as shown in FIG. 13, most endoscopes include a shaft 164 having a steerable distal end 128 and a hub or handle 162 which includes a visual channel 161 for connecting to a video screen 160 and a port 166 providing access to an inner working channel within the shaft 164. A power supply 159 can provide power to the endoscope 127 by way of a power cable 165. Dials, levers, or other mechanisms (not shown) will usually be provided on the handle 162 to allow an operator to selectively steer the distal end 128 of the endoscope 127 as is well known in the endoscopic arts. In use, wherein the ablation device 100 is coupled or connected to the endoscope 127, the combination can be introduced into and advanced within an alimentary tract. In an alternative embodiment, the step of advancing the ablation structure comprises advancing a catheter into the alimentary tract (not shown).

As shown in FIG. 4A, in one embodiment the method includes supporting the ablation structure (shown as an electrode 132) with the endoscope 127. In use, as illustrated in FIG. 4A, the ablation device 100, including the ablation structure (shown as an electrode 132), can be attached to the endoscope distal end 128 for support thereof. As discussed above in detail, in some embodiments the rotational support 116 further includes a base 112 constructed and arranged to connect the ablation device 100 to the endoscope 127. As such, the base 112 can provide an attachment point for support of the ablation device 100 by the endoscope 127.

In another method, the step of advancing an ablation device including an ablation structure into an alimentary tract includes advancing an endoscope into the alimentary tract and advancing the ablation device over the endoscope. For example, the endoscope can be positioned relative to an ablation target tissue after which the ablation device can be advanced over the outside of the endoscope for ablating the target tissue.

In another method the step of supporting the ablation device can include inserting an endoscope into the ablation device after the ablation device has been advanced into the alimentary tract. As disclosed in detail in co-pending U.S. patent application Ser. Nos. 11/286,257 and 11/286,444, filed Nov. 23, 2005, the full disclosure of which are fully incorporated herein by reference, variously adapted and configured ablation structures can fit within and be conveyed through an endoscope internal working channel. As such the ablation structure of the ablation device can alternatively be supported by an internal working channel of an endoscope. It is envisioned that combinations of any of the methods described herein for supporting the ablation device are possible.

In another embodiment of the method, where the ablation structure is at least one electrode, the step of activating the ablation structure can include supplying electrical energy to the electrode by way of electrical connections (see e.g., FIGS. 3A, 4A-B, 7A-B and 14A-C).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An ablation device comprising:
   an ablation element comprising a first end and a second end; and
   a support structure adapted to support the ablation element within an alimentary tract of a patient, the support structure comprising a longitudinal support with a longitudinal axis, the ablation element being positioned on a surface of the longitudinal support parallel to the longitudinal axis of the longitudinal support, and a rotational support, the rotational support comprising:

a base with a connecting element to connect the longitudinal support to an endoscope and a pin about which the longitudinal support is arranged such that it can rotate through an operative range of motion with respect to the longitudinal support's longitudinal axis, wherein, throughout the operative range of motion, a line orthogonal to the longitudinal axis of the longitudinal support and passing through the pin intersects the ablation element between the first and second end; and a movement resister configured to resist rotation of the longitudinal support.

2. The device of claim 1 wherein the movement resistor is coupled to the rotational support.

3. The device of claim 1 wherein the movement resistor is disposed between the longitudinal support and the base.

4. The device of claim 1 wherein the movement resister comprises a cantilever connected at its proximal portion to the base.

5. The device of claim 1 wherein the movement resistor comprises a spring.

6. The device of claim 1 wherein the movement resistor comprises a super elastic material.

7. The device of claim 1 wherein the movement resistor is arranged to resist rotational movement of the ablation element with respect to the longitudinal support's longitudinal axis.

8. The device of claim 1 wherein the movement resistor is configured to still permit force-induced rotation of the ablation element with respect to support structure's longitudinal axis.

9. The device of claim 1 wherein the movement resistor is configured to apply a tension to the longitudinal support such that it is biased to a neutral position wherein the longitudinal support is parallel to a longitudinal axis of an endoscope to which the longitudinal support is attached.

10. The device of claim 1 further comprising an endoscope to which the connecting element of the base is connected.

11. The device of claim 1, wherein the ablation element is non-planar.

12. A method of ablating tissue in an alimentary tract comprising:

advancing an ablation element into the alimentary tract, the ablation element comprising a first end and a second end;

supporting the ablation element on a surface of a longitudinal support having a longitudinal axis such that the ablation element is parallel to the longitudinal axis of the longitudinal support;

rotatably supporting the longitudinal support such that the longitudinal support can rotate about a pin through an operative range of motion with respect to the longitudinal support's longitudinal axis, wherein, throughout the operative range of motion, a line orthogonal to the longitudinal axis of the longitudinal support and passing through the pin intersects the ablation element between the first and second end; and resisting rotation of the longitudinal support away from a neutral position wherein the longitudinal axis of the longitudinal support is parallel to a longitudinal axis of an endoscope to which the longitudinal support is connected.

13. The method of claim 12 wherein the resisting rotation step comprises resisting rotation in response to a force deflecting the longitudinal support away from the neutral position.

14. The method of claim 12, further comprising forcing the rotation of the longitudinal support about its longitudinal axis away from the neutral position during the resisting step.

15. The method of claim 14 further comprising returning the longitudinal axis of the longitudinal support to the neutral position after the rotating step.

16. The method of claim 12 wherein resisting rotation comprises passively resisting rotation.

17. The method of claim 12 wherein resisting rotation comprises resisting rotation with a spring.

18. The method of claim 17 wherein resisting rotation with the spring comprises resisting with a cantilever spring.

19. The method of claim 12 wherein resisting rotation comprises reducing a profile of an ablation device comprising the ablation element during the advancing step.

* * * * *